(12) United States Patent
Park et al.

(10) Patent No.: US 9,178,163 B2
(45) Date of Patent: Nov. 3, 2015

(54) COMPOUND COMPRISING A FIVE-MEMBERED HETERO RING, AN ORGANIC ELECTRICAL ELEMENT USING SAME AND A TERMINAL THEREOF

(71) Applicant: Duk San Neolux Co., Ltd., Chungcheongnam-do (KR)

(72) Inventors: Junghwan Park, Seoul (KR); Daesung Kim, Gyeonggi-do (KR); Heesun Ji, Seoul (KR); Soungyun Mun, Gyeonggi-do (KR); Sunhee Lee, Chungcheongnam-do (KR); Bumsung Lee, Chungcheongnam-do (KR)

(73) Assignee: DUK SAN NEOLUX CO., LTD., Cheonan-si, Chungcheongnam-do (KR)

( * ) Notice: Subject to any disclaimer, the term of this patent is extended or adjusted under 35 U.S.C. 154(b) by 0 days.

(21) Appl. No.: 14/685,376

(22) Filed: Apr. 13, 2015

(65) Prior Publication Data

US 2015/0221873 A1    Aug. 6, 2015

Related U.S. Application Data

(63) Continuation-in-part of application No. 13/699,040, filed as application No. PCT/KR2011/003862 on May 26, 2011, now Pat. No. 9,005,779.

(30) Foreign Application Priority Data

May 26, 2010    (KR) .................. 10-2010-0049325

(51) Int. Cl.
*H01L 51/50* (2006.01)
*H01L 51/00* (2006.01)
*C07D 495/04* (2006.01)
*H01L 51/52* (2006.01)

(52) U.S. Cl.
CPC .......... *H01L 51/0061* (2013.01); *C07D 495/04* (2013.01); *H01L 51/006* (2013.01); *H01L 51/0052* (2013.01); *H01L 51/0058* (2013.01); *H01L 51/0071* (2013.01); *H01L 51/0072* (2013.01); *H01L 51/0074* (2013.01); *H01L 51/506* (2013.01); *H01L 51/5012* (2013.01); *H01L 51/5072* (2013.01); *H01L 51/5088* (2013.01); *H01L 51/5092* (2013.01); *H01L 51/5206* (2013.01); *H01L 51/5221* (2013.01); *H01L 2251/301* (2013.01); *H01L 2251/308* (2013.01)

(58) Field of Classification Search
CPC ........... C09K 11/06; C09K 2211/1011; C09K 2211/1029; C09K 2211/1044; C09K 2211/1048; C09K 2211/1051; C09K 2211/1055; C09K 2211/1416; C09K 2211/145; C09K 2211/1458; C09K 2211/1466
USPC .................. 428/690, 917; 313/504, 505, 506; 548/304.1, 418, 440, 444; 257/40, 257/E51.05, E51.026, E51.032, E51.052; 564/26, 426, 432, 434
See application file for complete search history.

*Primary Examiner* — Gregory Clark
(74) *Attorney, Agent, or Firm* — Vorys, Sater, Seymour and Pease LLP; Mihsun Koh

(57) ABSTRACT

A compound having a five-membered hetero ring, an organic electrical element using the same and a terminal thereof. An organic electric element includes a first electrode, a second electrode, and an organic material layer between the first electrode and the second electrode. The organic material layer includes the compound. When the organic electric element includes the compound in an organic material layer, luminous efficiency, stability, and life span can be improved.

10 Claims, 6 Drawing Sheets

COMPOUND COMPRISING A FIVE-MEMBERED HETERO RING, AN ORGANIC ELECTRICAL ELEMENT USING SAME AND A TERMINAL THEREOF

CROSS REFERENCE TO RELATED APPLICATIONS AND CLAIM OF PRIORITY

The present application is a continuation-in-part application to U.S. patent application Ser. No. 13/699,040, filed Nov. 20, 2012, which is a National Phase application under U.S.C. §371 of International Application No. PCT/KR2011/003862, filed May 26, 2011, which claims priority to Korean Patent Application No. 10-2010-0049325 filed May 26, 2010, entire contents of which are incorporated herein by reference.

BACKGROUND

1. Technical Field

The present invention relates to a compound including a five-membered hetero ring, an organic electrical element using the same, and a terminal including the organic electrical element.

2. Background Art

In general, an organic light emitting phenomenon refers to a phenomenon in which electric energy is converted into light energy by means of an organic material. An organic electrical element utilizing the organic light emitting phenomenon usually has a structure including an anode, a cathode, and an organic material layer interposed therebetween. Here, in many cases, the organic material layer may have a multilayered structure including multiple layers made of different materials in order to improve the efficiency and stability of an organic electrical element, and for example, may include a hole injection layer, a hole transport layer, a light emitting layer, an electron transport layer, an electron injection layer, and the like.

A material used as an organic material layer in an organic electrical element may be classified into a light emitting material and a charge transport material, for example, a hole injection material, a hole transport material, an electron transport material, an electron injection material, and the like according to its function. Further, the light emitting material may be divided into a high molecular weight type and a low molecular weight type according to its molecular weight, and may also be divided into a fluorescent material derived from electronic excited singlet states and a phosphorescent material derived from electronic excited triplet states according to its light emitting mechanism. Further, the light emitting material may be divided into blue, green, and red light emitting materials, and yellow and orange light emitting materials required for better natural color reproduction according to its light emitting color.

Meanwhile, when only one material is used as a light emitting material, there occur problems of shift of a maximum luminescence wavelength to a longer wavelength due to intermolecular interactions and lowering of the efficiency of a corresponding element due to a deterioration in color purity or a reduction in luminous efficiency. On account of this, a host/dopant system may be used as the light emitting material in order to enhance the color purity and increase the luminous efficiency through energy transfer. This is based on the principle that if a small amount of dopant having a smaller energy band gap than a host forming a light emitting layer is mixed in the light emitting layer, then excitons generated in the light emitting layer are transported to the dopant, thus emitting light with high efficiency. With regard to this, since the wavelength of the host is shifted to the wavelength band of the dopant, light having a desired wavelength can be obtained according the type of the dopant.

In order to allow an organic electrical element to fully exhibit the above-mentioned excellent features, it should be prerequisite to support a material constituting an organic material layer in the element, for example, a hole injection material, a hole transport material, a light emitting material, an electron transport material, an electron injection material, or the like, by a stable and efficient material. However, such a stable and efficient organic material layer material for an organic electrical element has not yet been fully developed. Accordingly, there is a continuous need to develop new materials for an organic material layer.

SUMMARY

In order to solve the above-mentioned problems occurring in the prior art, embodiments of the present invention have led to the discovery of a compound including a five-membered hetero ring. Further, it was found that when this compound is employed in an organic electrical element, the element can be significantly improved in luminous efficiency, stability, and life span.

Accordingly, an aspect of the present invention is to provide a compound including a five-membered hetero ring, an organic electrical element using the same, and a terminal including the organic electrical element.

In accordance with an aspect of the present invention, there is provided a compound represented by Formula below.

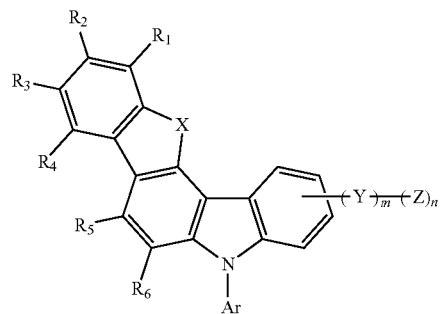

The inventive compound including two or more five-membered hetero rings has proved to be a material that can not only provide high efficiency and enhance color purity, but can also improve driving voltage in an organic electrical element. Accordingly, the present invention provides a compound including two or more five-membered hetero rings as core components, an organic electrical element using the same, and a terminal including the organic electrical element.

The inventive compound, which is synthesized by a compound including two or more five-membered hetero rings, is useful as a hole injection material, a hole transport material, a light emitting material, and/or an electron transport material appropriate for both fluorescent and phosphorescent elements of all colors such as red, green, blue, and white.

DETAILED DESCRIPTION

Figure 1:
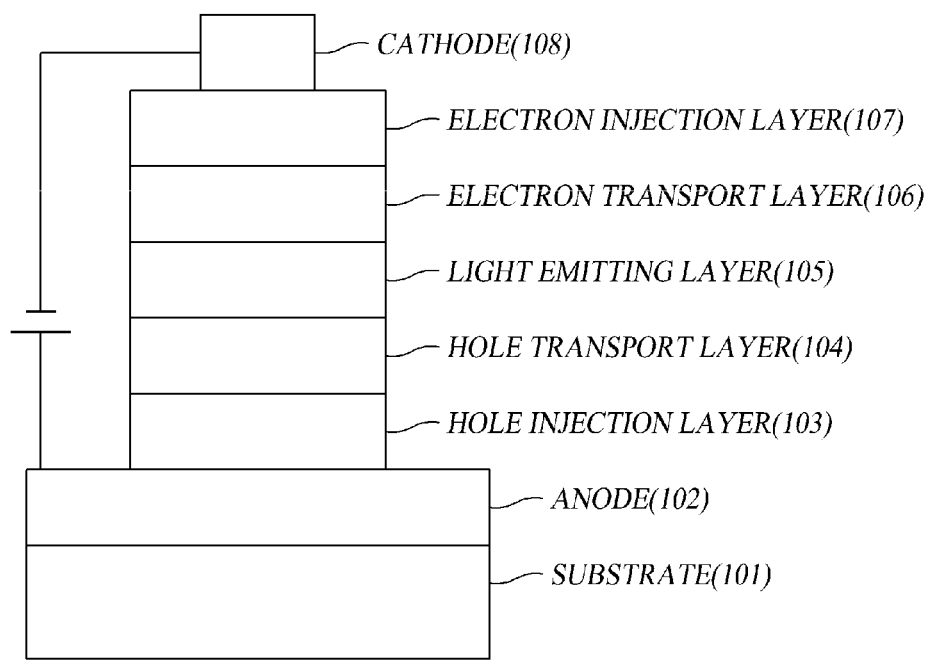
FIGS. 1 to 6 illustrate examples of an organic light emitting diode in which a compound according to the present invention may be employed.

Hereinafter, some embodiments of the present invention will be described in detail with reference to the accompanying illustrative drawings. In designation of reference numerals to components in respective drawings, it should be noted that the same elements will be designated by the same reference numerals although they are shown in different drawings. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used to define an essence, order or sequence of a corresponding component but used merely to distinguish the corresponding component from other component(s). It should be noted that if it is described in the specification that one component is "connected," "coupled" or "joined" to another component, a third component may be "connected," "coupled," and "joined" between the first and second components, although the first component may be directly connected, coupled or joined to the second component.

An aspect of the present invention provides a compound represented by Formula 1 below.

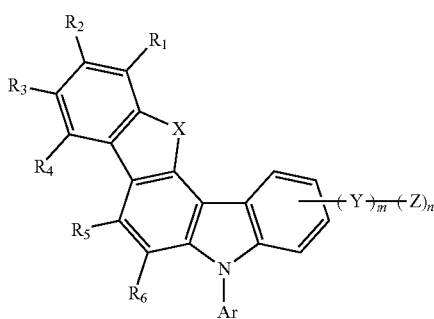

[Formula 1]

(1) $R_1$, $R_2$, $R_3$, $R_4$, $R_5$, and $R_6$ are each independently a hydrogen atom, a halogen atom, a cyano group, an alkoxy group, a thiol group, a substituted or unsubstituted C1 to C50 alkyl group, a substituted or unsubstituted C1 to C50 alkoxy group, a substituted or unsubstituted C1 to C50 alkenyl group, a substituted or unsubstituted C5 to C60 arylene group, a substituted or unsubstituted C5 to C60 aryl group, a substituted or unsubstituted C5 to C60 aryloxy group, a substituted or unsubstituted C1 to C50 alkyl group including at least one of sulfur (S), nitrogen (N), oxygen (O), phosphorous (P), and silicon (Si), a substituted or unsubstituted C5 to C60 heteroaryl group including at least one of sulfur (S), nitrogen (N), oxygen (O), phosphorous (P) and silicon (Si), or a substituted or unsubstituted C5 to C60 heteroaryloxy group including at least one of sulfur (S), nitrogen (N), oxygen (O), phosphorous (P) and silicon (Si).

(2) $R_1$ and $R_2$, $R_2$ and $R_3$, $R_3$ and $R_4$, and $R_5$ and $R_6$ each may form a substituted or unsubstituted, saturated or unsaturated aliphatic ring or a hetero ring having N, O, or S as a hetero atom together with an adjacent group.

(3) X is at least one of sulfur (S), oxygen (O), and silicon (Si).

(4) Ar is a hydrogen atom, a substituted or unsubstituted C1 to C50 alkyl group, a substituted or unsubstituted C1 to C50 alkenyl group, a substituted or unsubstituted C5 to C60 arylene group, a substituted or unsubstituted C5 to C60 aryl group, a substituted or unsubstituted C5 to C60 aryloxy group, a substituted or unsubstituted C1 to C50 alkyl group including at least one of sulfur (S), nitrogen (N), oxygen (O), phosphorous (P), and silicon (Si), a substituted or unsubstituted C5 to C60 heteroaryl group including at least one of sulfur (S), nitrogen (N), oxygen (O), phosphorous (P) and silicon (Si), or a substituted or unsubstituted C5 to C60 heteroaryloxy group including at least one of sulfur (S), nitrogen (N), oxygen (O), phosphorous (P) and silicon (Si).

(5) Y is a substituted or unsubstituted C1 to C50 alkyl group, a substituted or unsubstituted C1 to C50 alkenyl group, a substituted or unsubstituted C5 to C60 arylene group, a substituted or unsubstituted C5 to C60 aryl group, a substituted or unsubstituted C5 to C60 aryloxy group, a substituted or unsubstituted C1 to C50 alkyl group including at least one of sulfur (S), nitrogen (N), oxygen (O), phosphorous (P), and silicon (Si), a substituted or unsubstituted C5 to C60 heteroaryl group including at least one of sulfur (S), nitrogen (N), oxygen (O), phosphorous (P) and silicon (Si), or a substituted or unsubstituted C5 to C60 heteroaryloxy group including at least one of sulfur (S), nitrogen (N), oxygen (O), phosphorous (P) and silicon (Si).

(6) Z is S, $NR_7R_8$, $OR_9$, $PR_{10}R_{11}$ or $POR_{10}R_{11}$, or $SiR_{12}$ wherein $R_7$, $R_8$, $R_9$, $R_{10}$, $R_{11}$, and $R_{12}$ are each independently a substituted or unsubstituted C5 to C60 aryl group or a substituted or unsubstituted C5 to C60 heteroaryl group including at least one of sulfur (S), nitrogen (N), oxygen (O), phosphorous (P) and silicon (Si). Preferably, when m is the ingeger of 0, $R_7$ and $R_8$ may not bond to each other to form a ring structure.

(7) m has an integer from 0 to 2, and n has an integer from 1 to 2.

Specific examples of a compound including five-membered hetero rings according to an embodiment of the present invention, represented by Formula 1, may include compounds represented by Formulas 2 to 7 below, but the present invention is not limited thereto.

Another aspect of the present invention provides a compound represented by Formula 2 below.

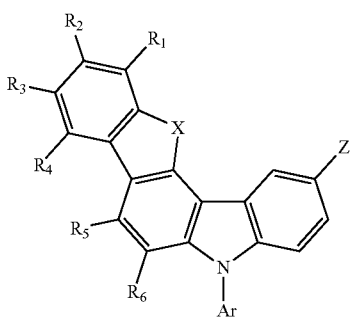

[Formula 2]

Yet another aspect of the present invention provides a compound represented by Formula 3 below.

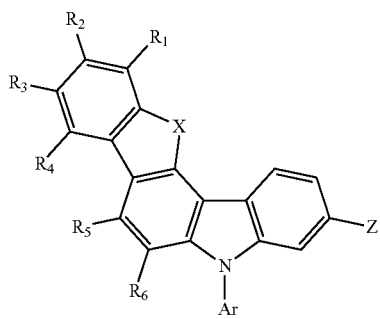

[Formula 3]

Still yet another aspect of the present invention provides a compound represented by Formula 4 below.

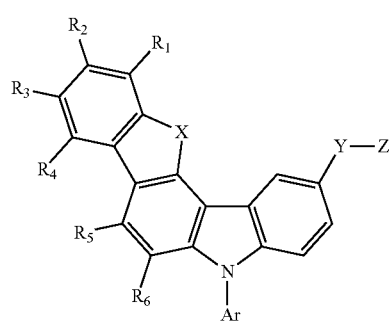

[Formula 4]

Still yet another aspect of the present invention provides a compound represented by Formula 5 below.

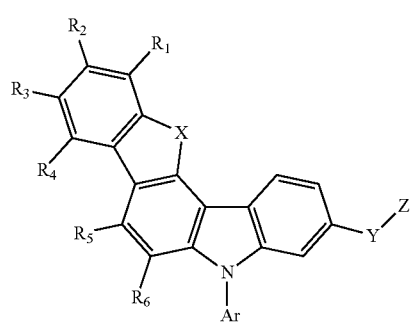

[Formula 5]

Still yet another aspect of the present invention provides a compound represented by Formula 6 below.

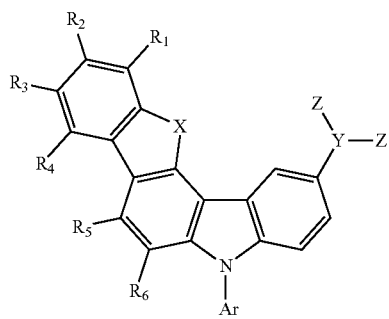

[Formula 6]

Still yet another aspect of the present invention provides a compound represented by Formula 7 below.

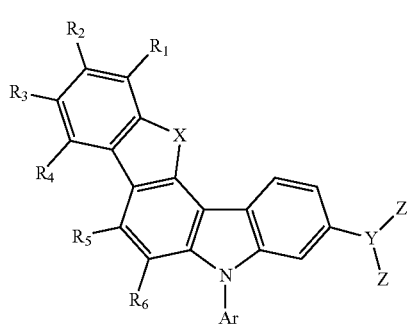

[Formula 7]

Compounds represented by Formulas 2 to 7 may be further represented by Formulas 8 to 13 below, but the present invention is not limited thereto.

[Formula 8]

Compound 1-1

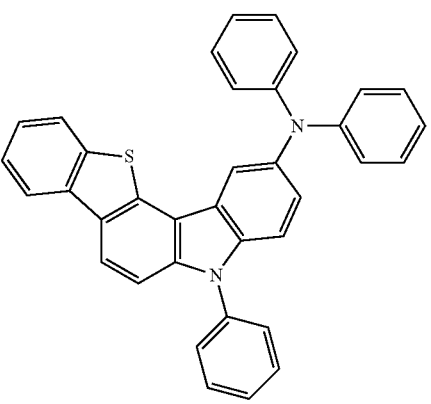

Compound 1-2
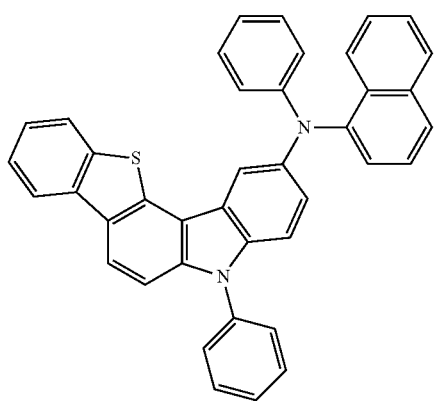
Compound 1-3
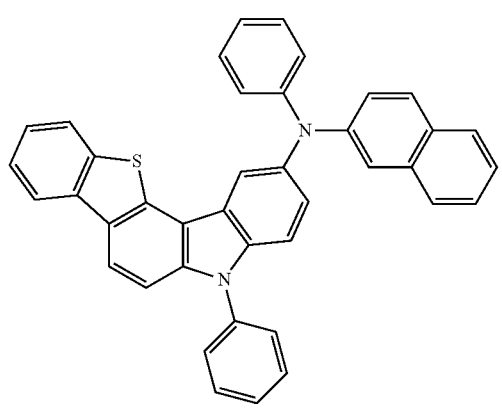
Compound 1-4
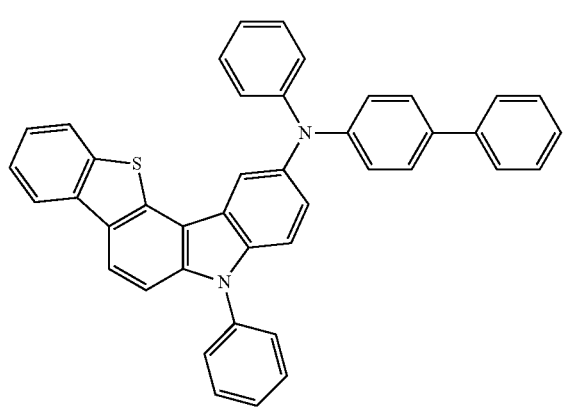
Compound 1-5
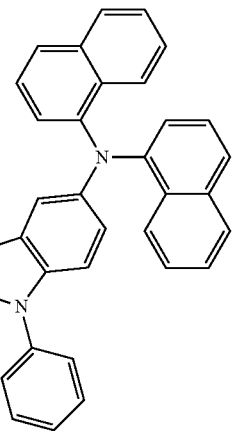
Compound 1-6
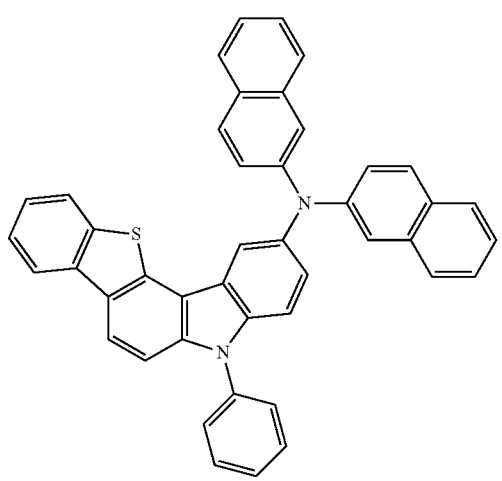
Compound 1-7
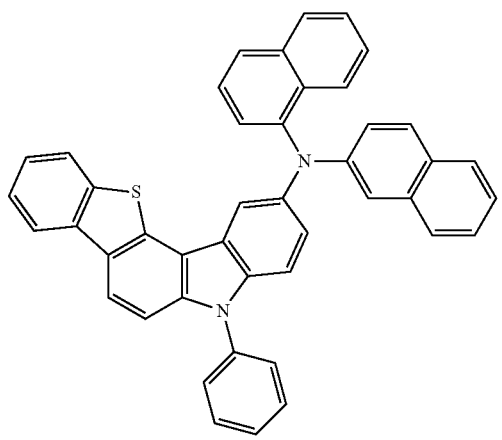

Compound 1-8
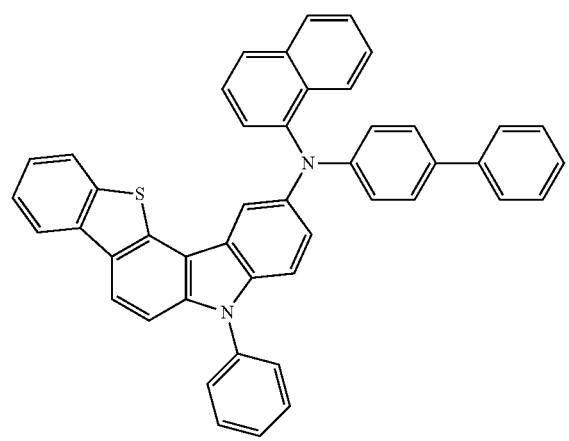
Compound 1-9
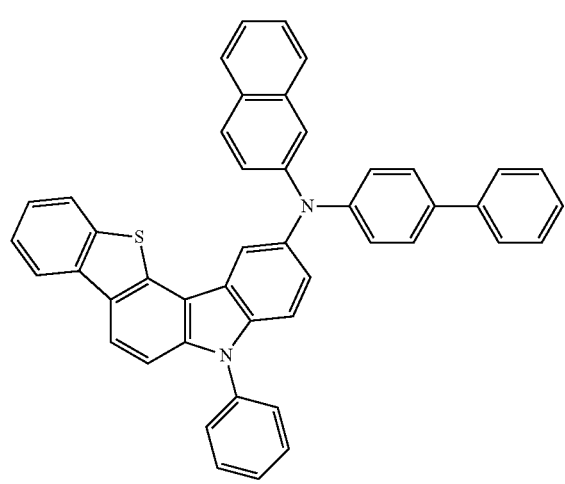
Compound 1-10
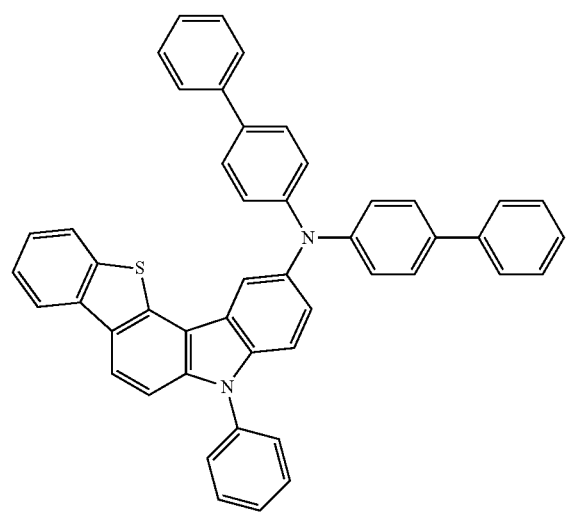
Compound 1-11
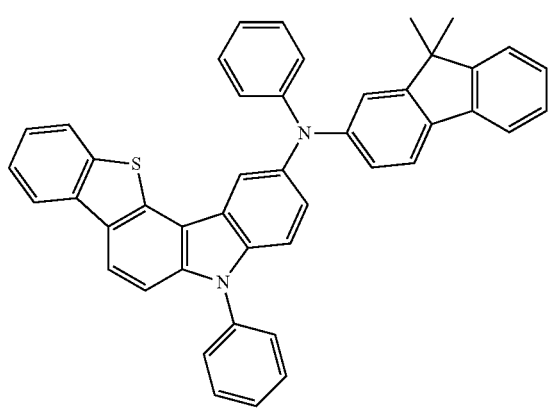
Compound 1-12
Compound 1-13
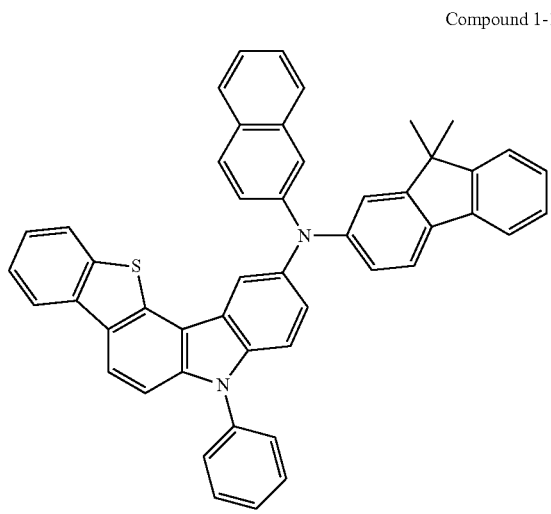

-continued

Compound 1-14

Compound 1-15

Compound 1-16

Compound 1-17

Compound 1-18

Compound 1-19

Compound 1-20
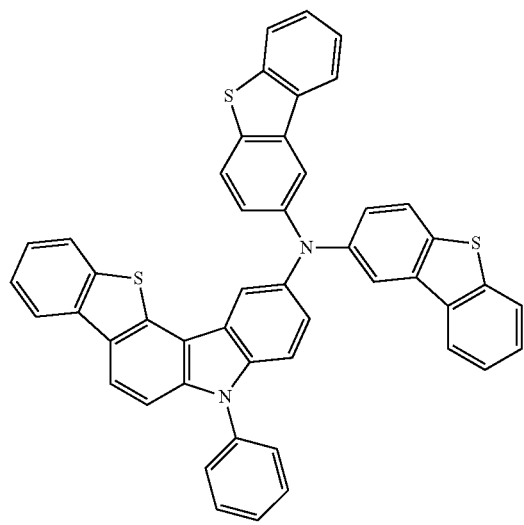
Compound 1-21
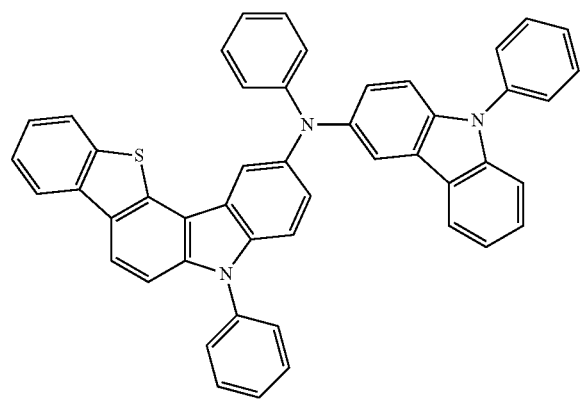
Compound 1-22
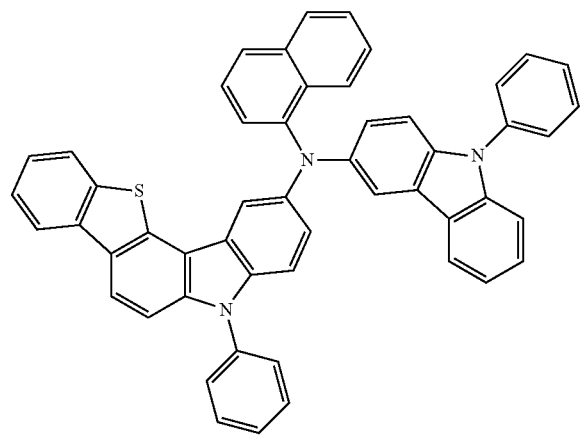
Compound 1-23
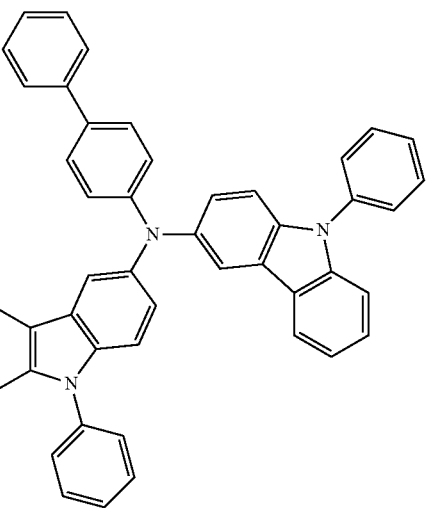
Compound 1-24
Compound 1-25
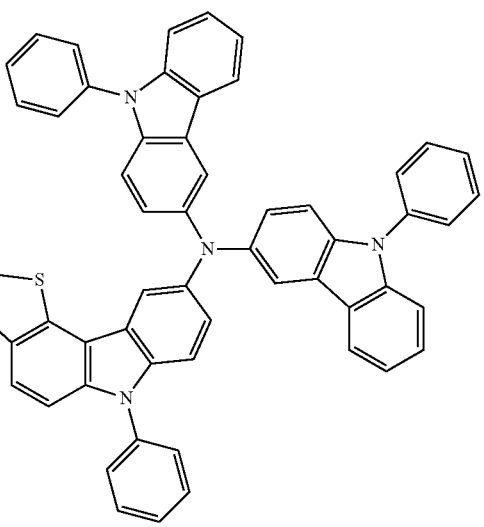

Compound 1-26
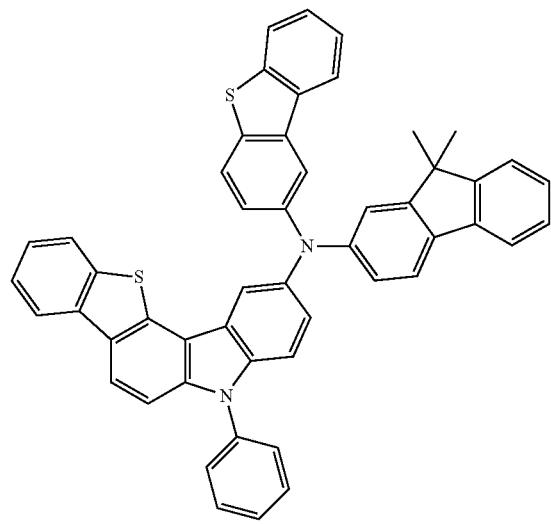
Compound 1-27
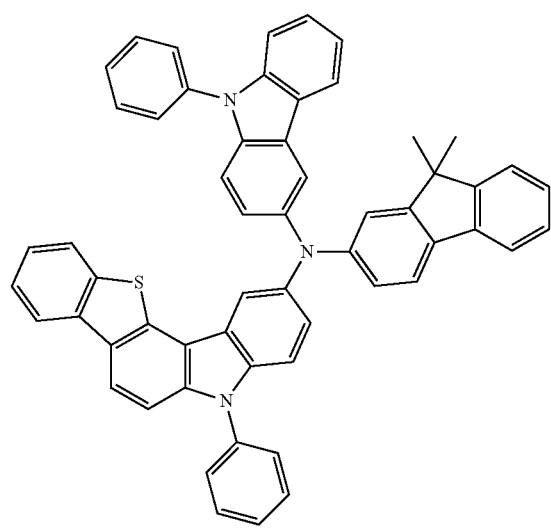
Compound 1-28
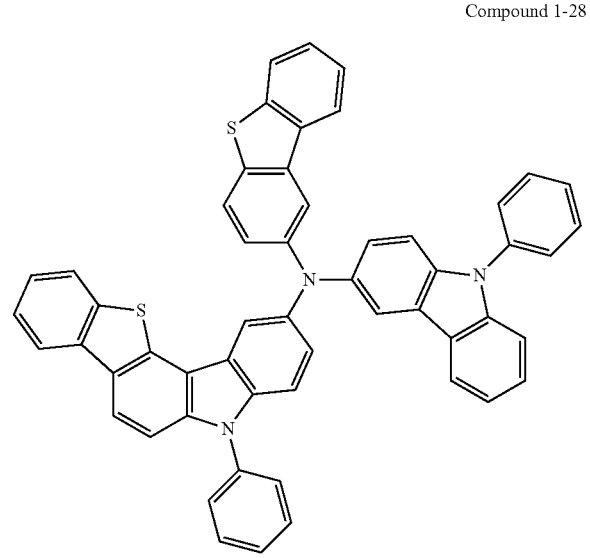
Compound 1-29
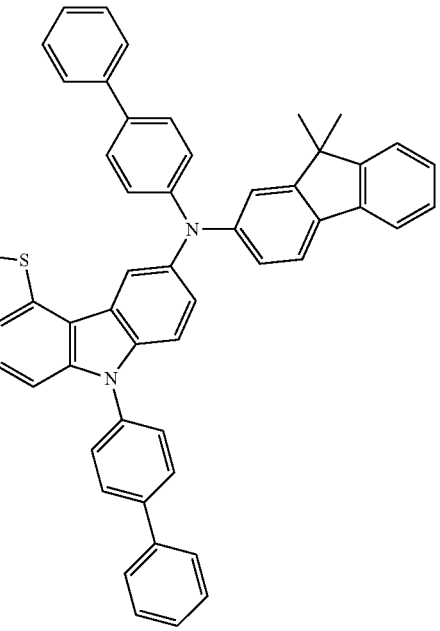
Compound 1-30
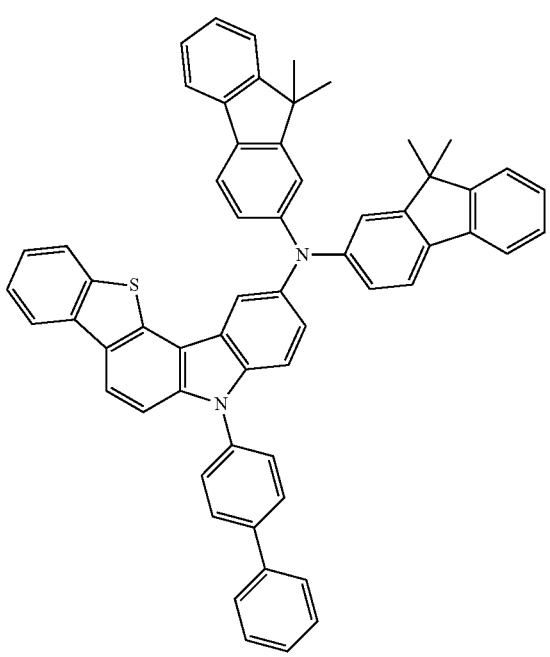

[Formula 9]
Compound 2-1
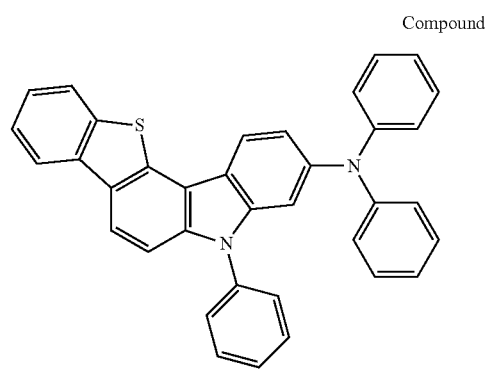
Compound 2-2
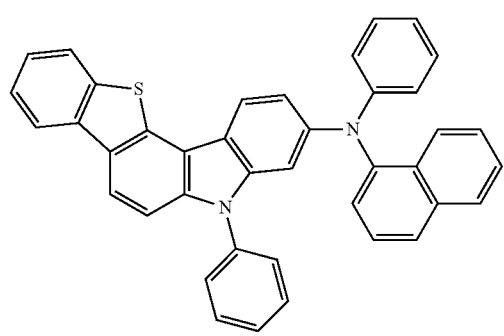
Compound 2-3
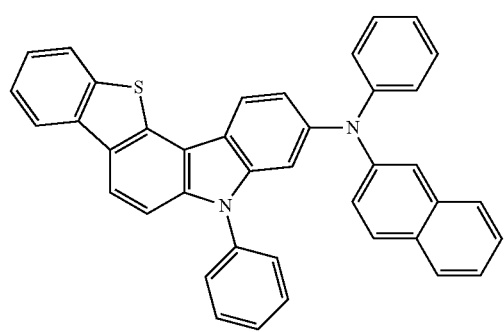
Compound 2-4
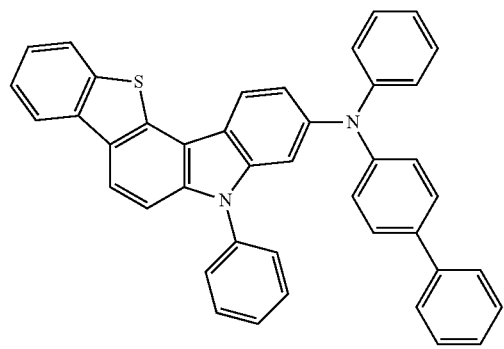
Compound 2-5
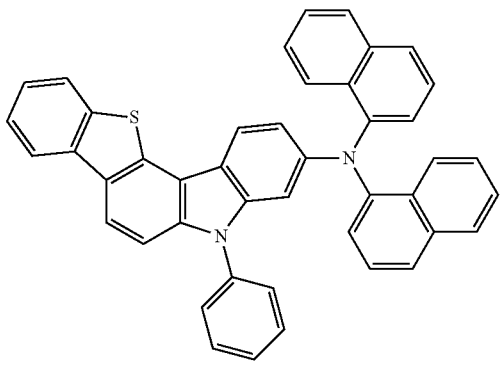
Compound 2-6
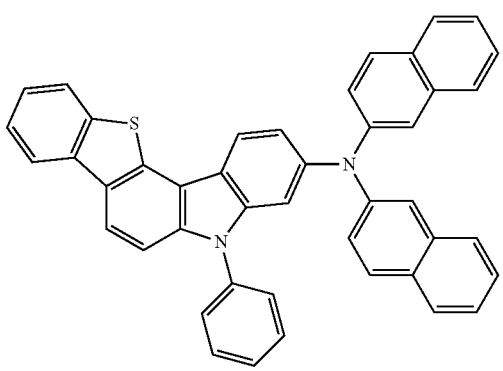
Compound 2-7
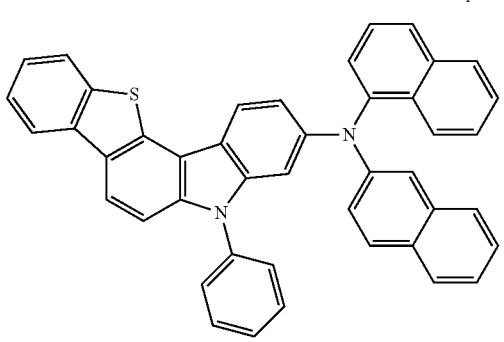
Compound 2-8
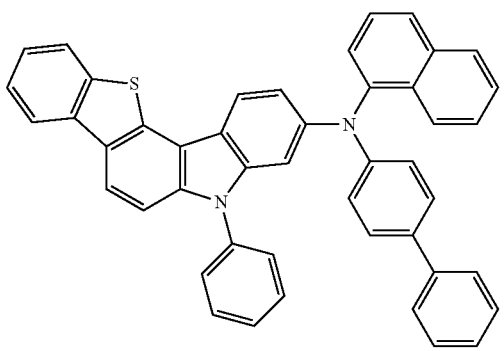

Compound 2-9
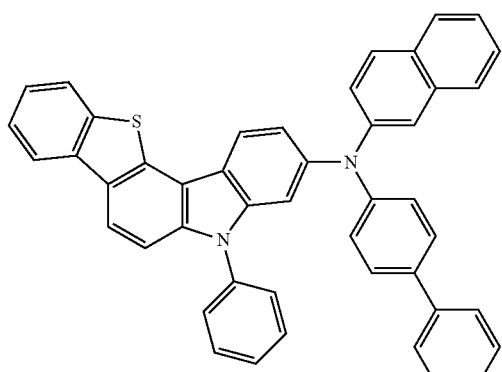
Compound 2-10
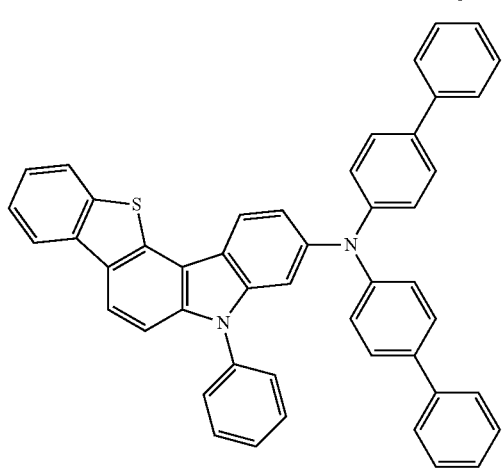
Compound 2-11
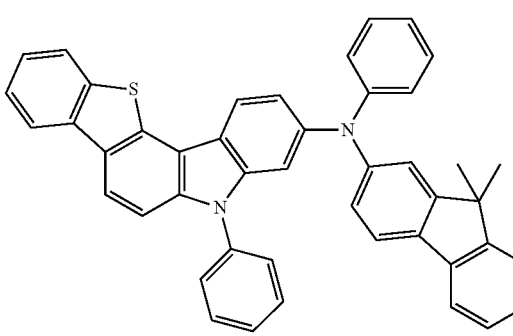
Compound 2-12
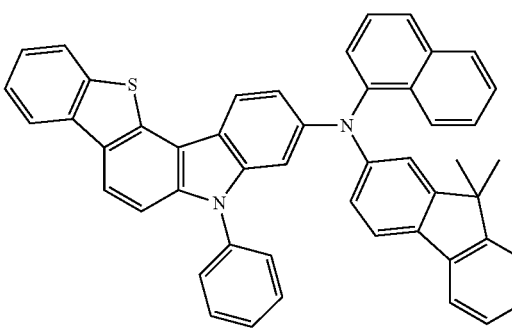
Compound 2-13
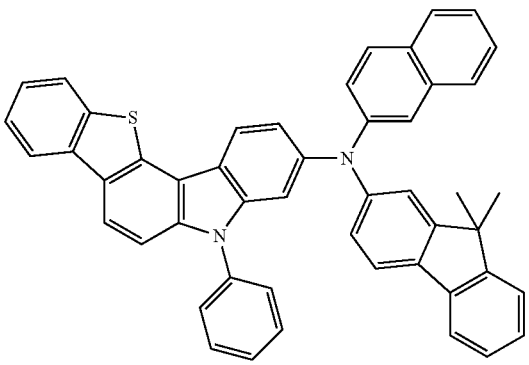
Compound 2-14
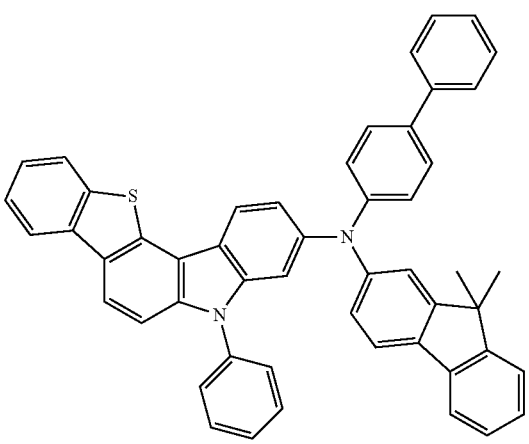
Compound 2-15
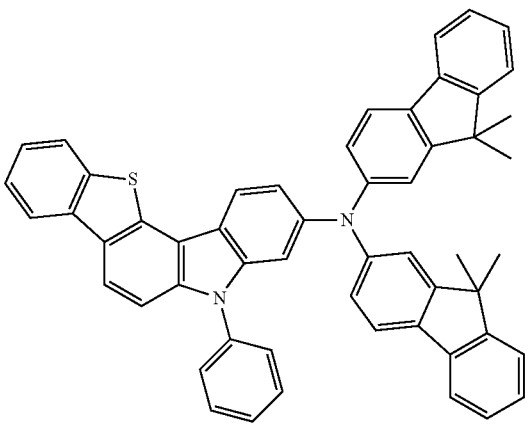
Compound 2-16
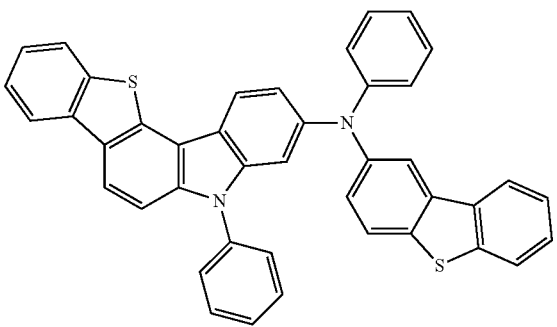

Compound 2-17
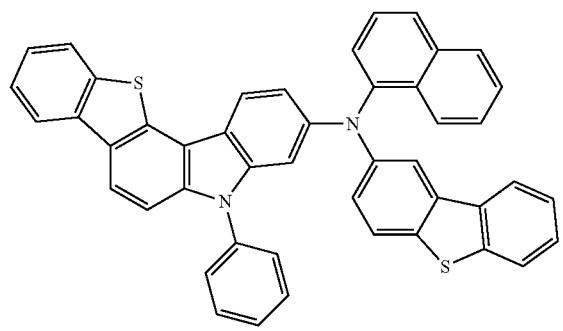
Compound 2-18
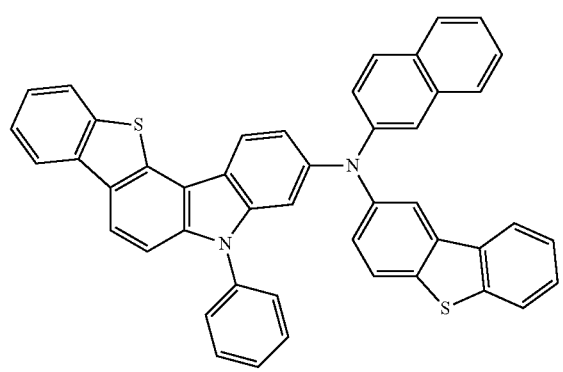
Compound 2-19
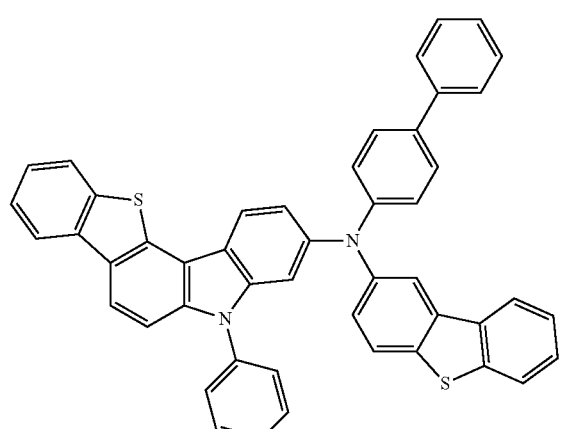
Compound 2-20
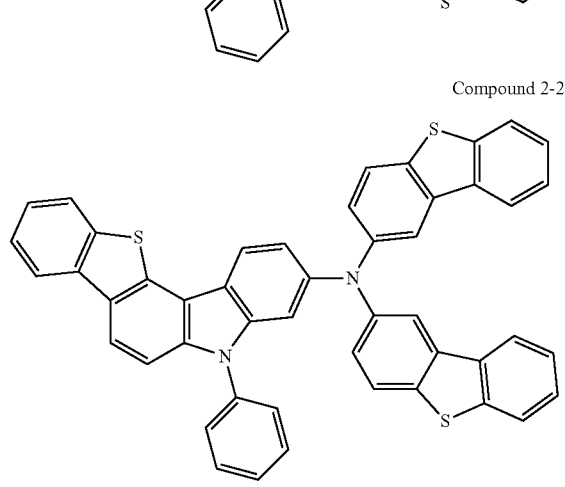
Compound 2-21
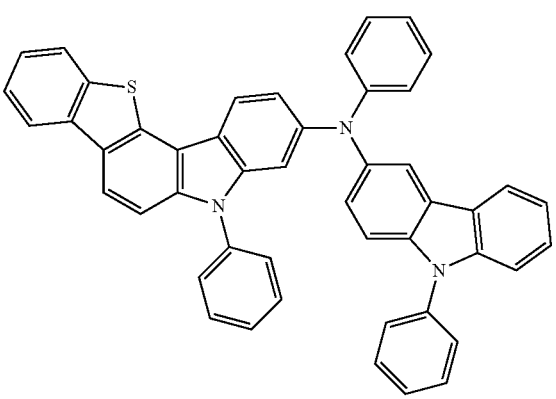
Compound 2-22
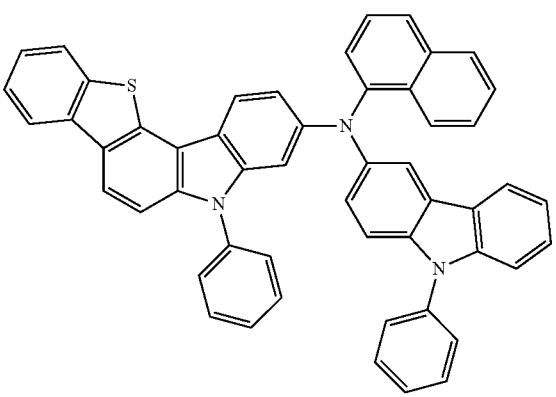
Compound 2-23
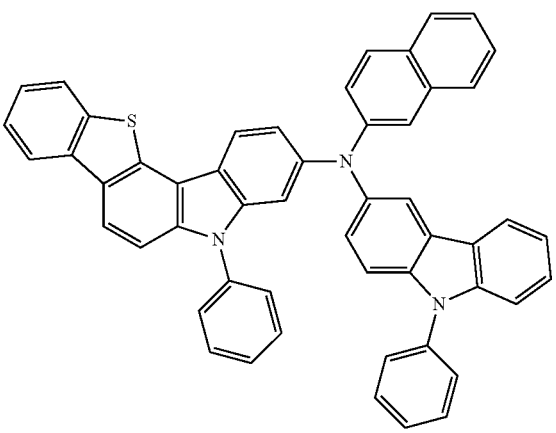

Compound 2-24
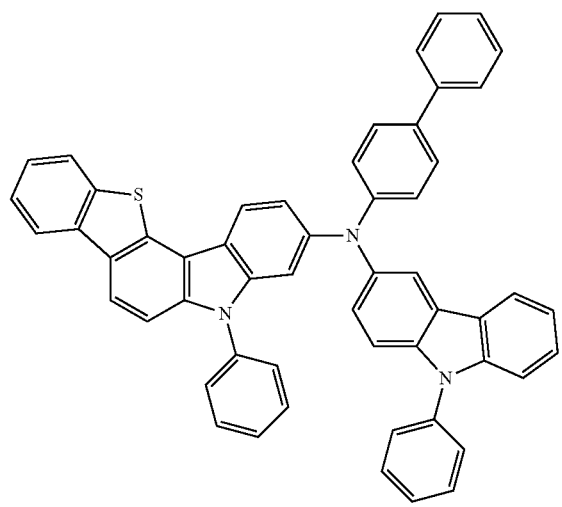
Compound 2-25
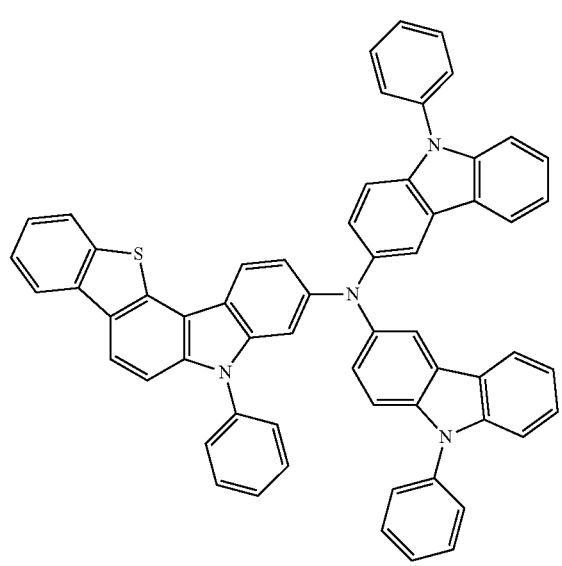
Compound 2-26
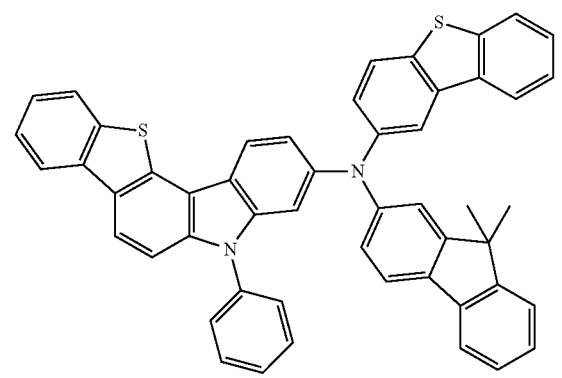
Compound 2-27
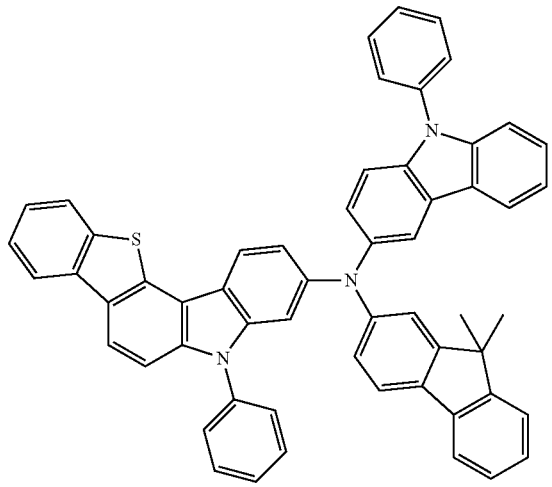
Compound 2-28
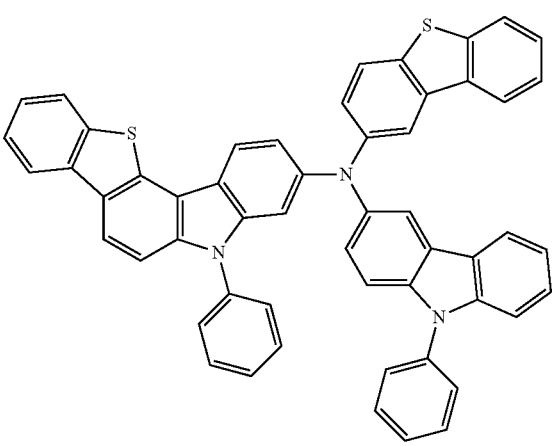
Compound 2-29
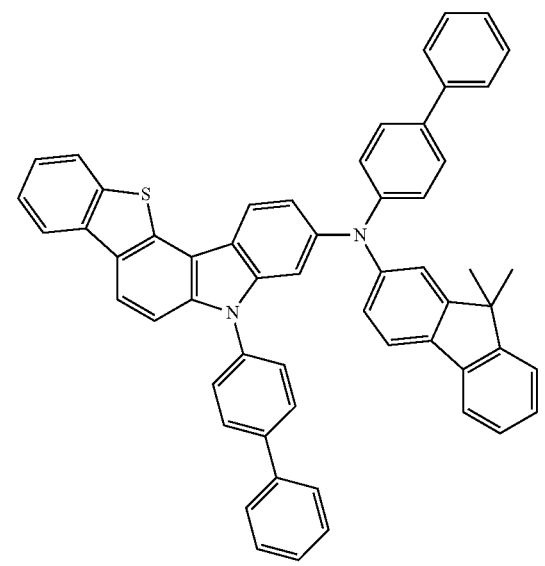

Compound 2-30
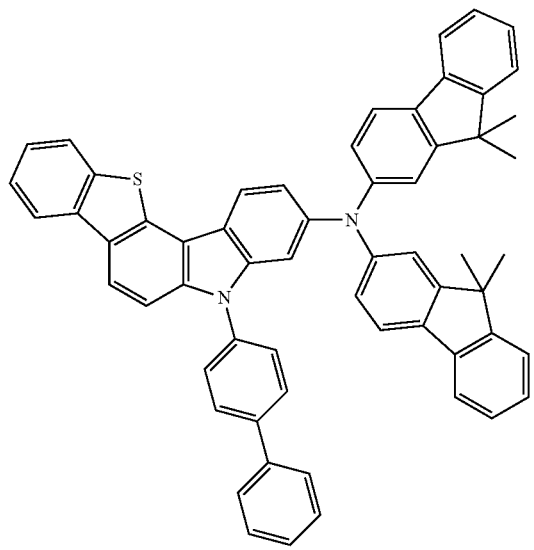
[Formula 10]
Compound 3-1
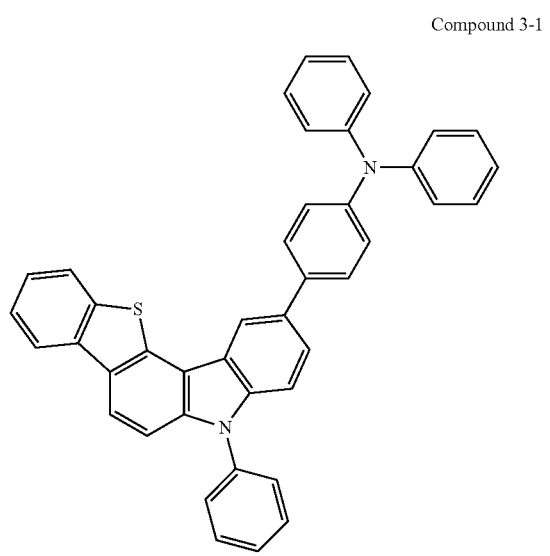
Compound 3-2
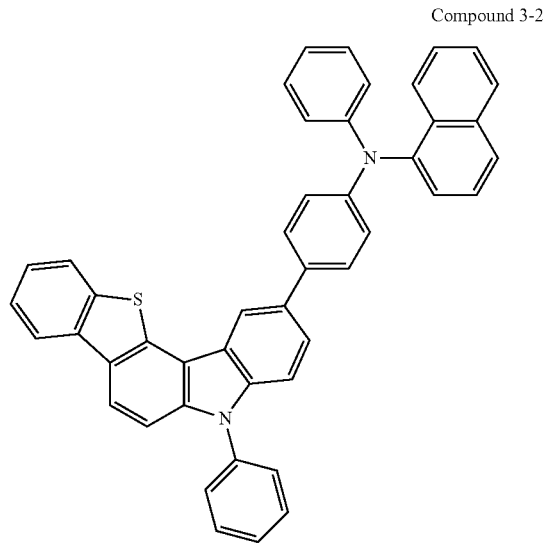
Compound 3-3
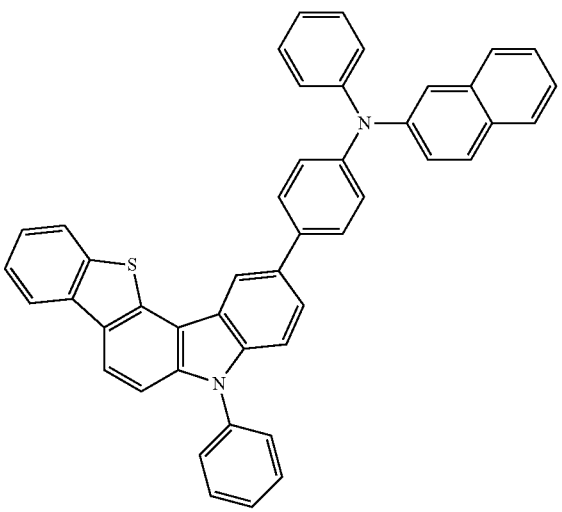
Compound 3-4
Compound 3-5
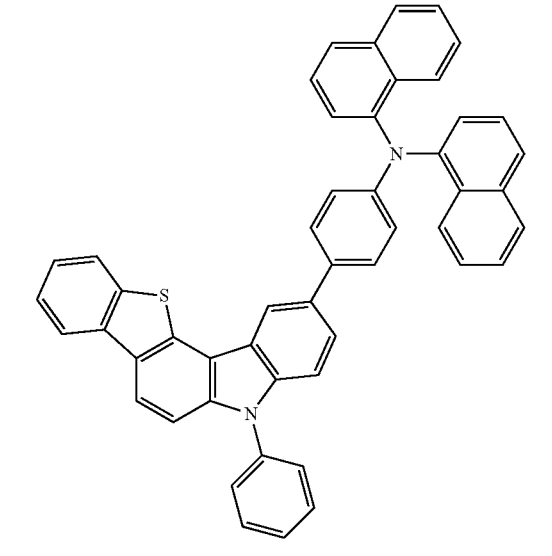

Compound 3-6
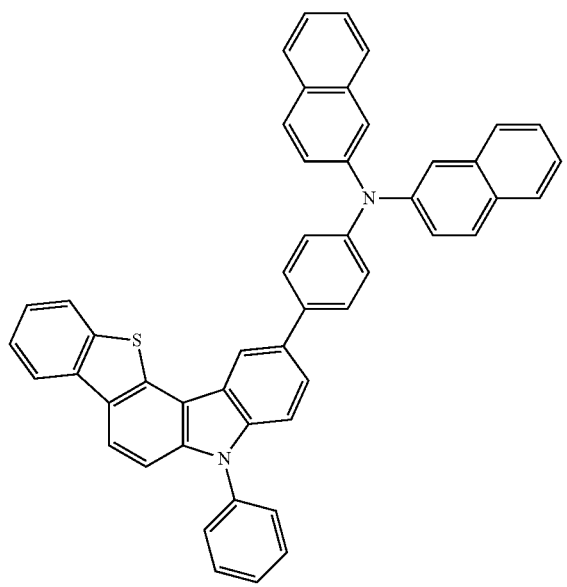
Compound 3-7
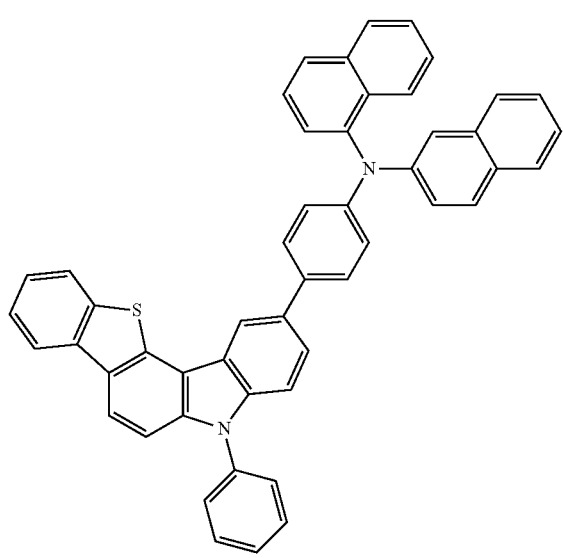
Compound 3-8
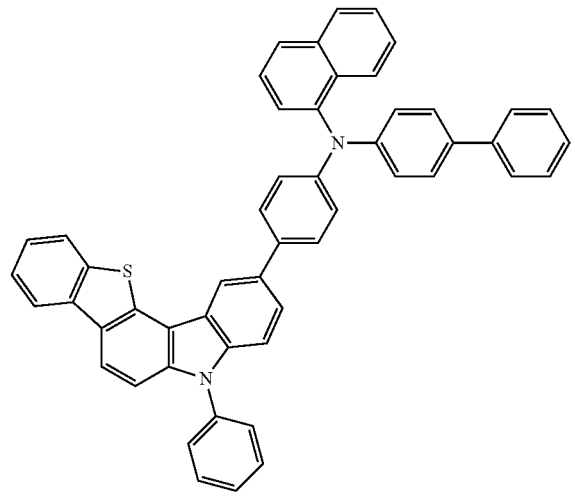
Compound 3-9
Compound 3-10
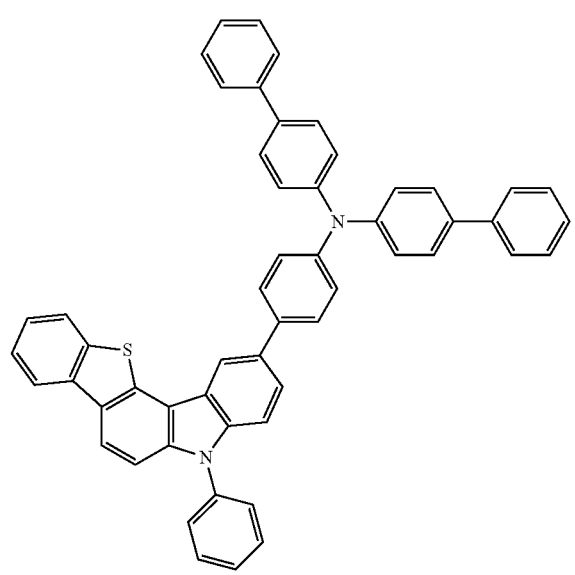

Compound 3-11
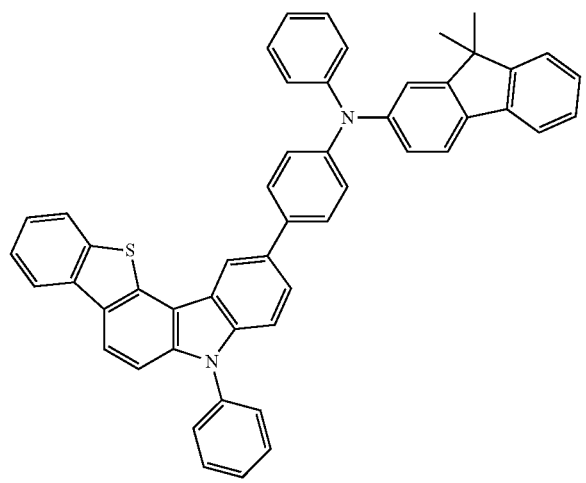
Compound 3-12
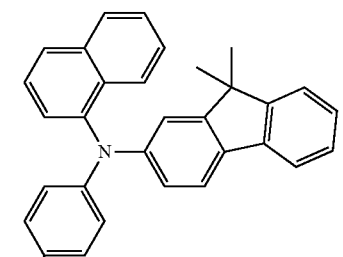
Compound 3-13
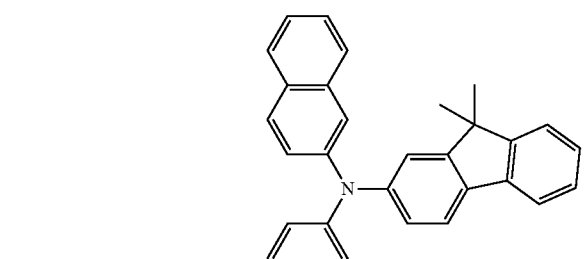
Compound 3-14
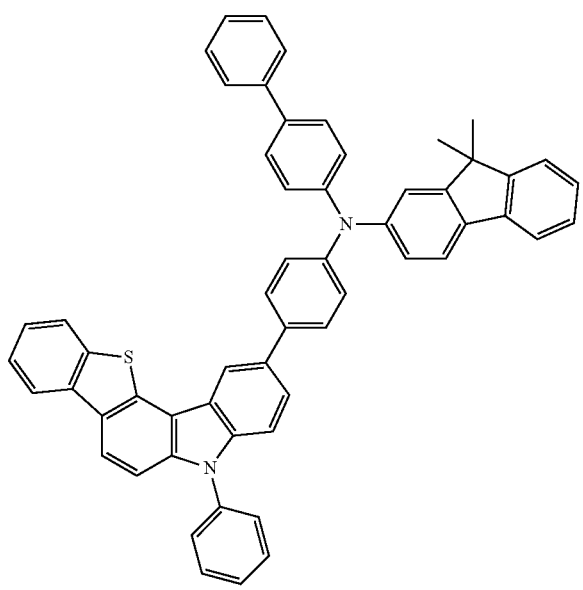
Compound 3-15
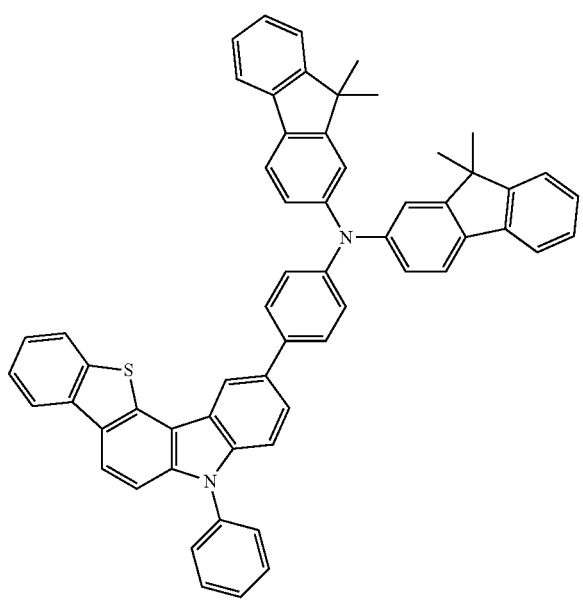

-continued
Compound 3-16
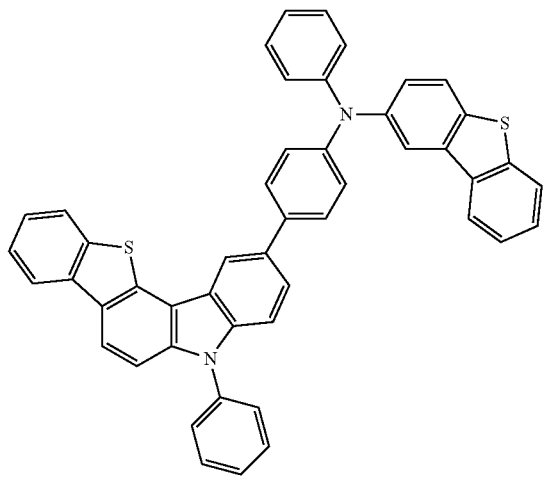
Compound 3-17
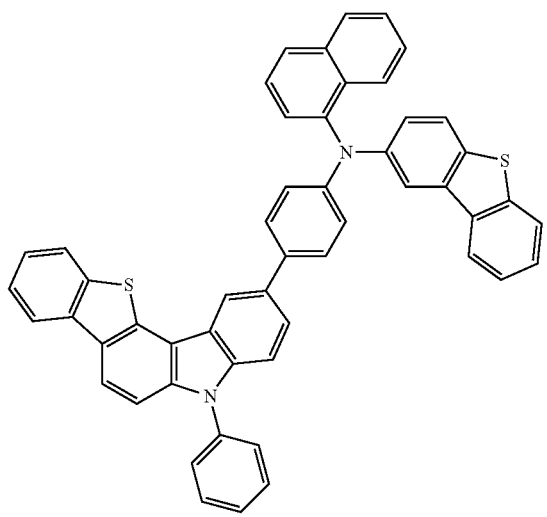
Compound 3-18
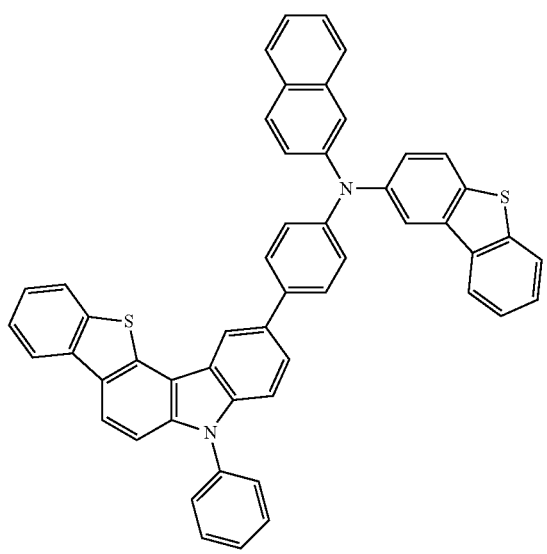
Compound 3-19
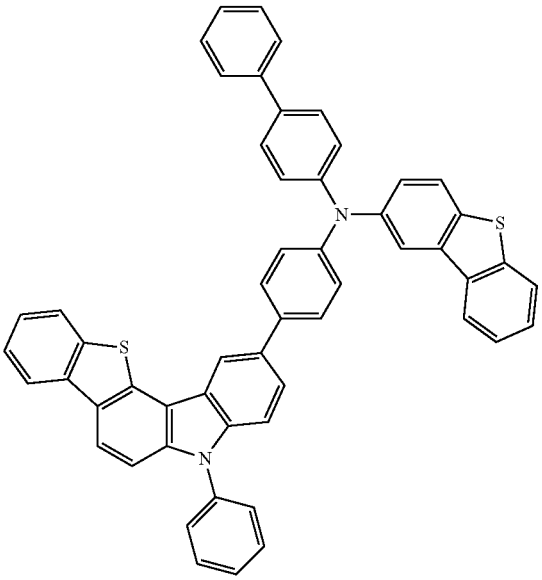
Compound 3-20
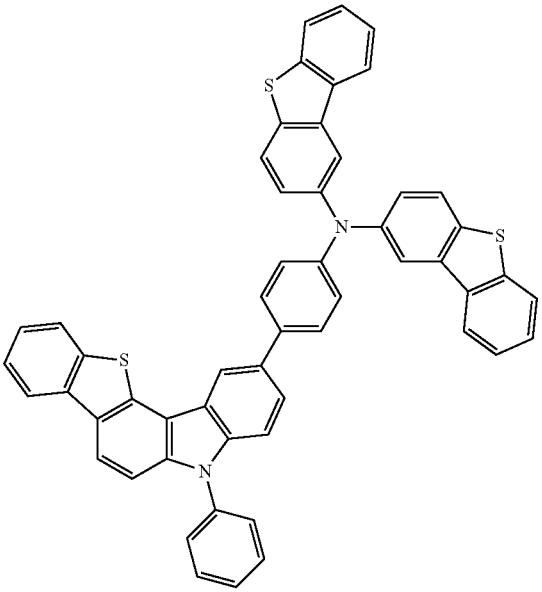

-continued
Compound 3-21
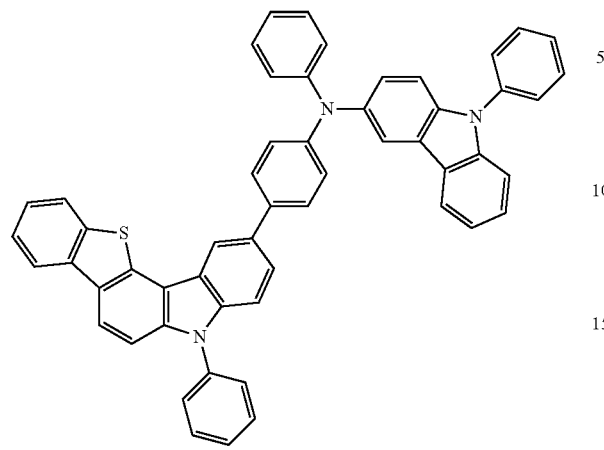
Compound 3-22
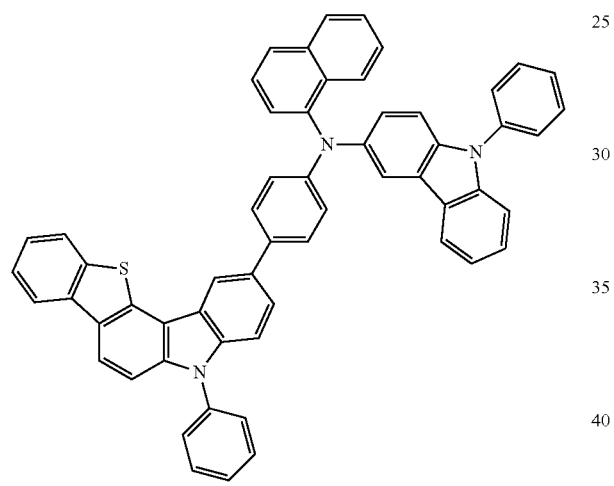
Compound 3-23
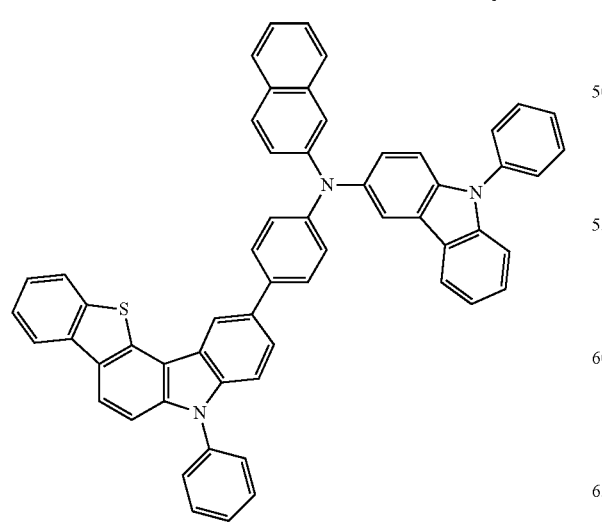
Compound 3-24
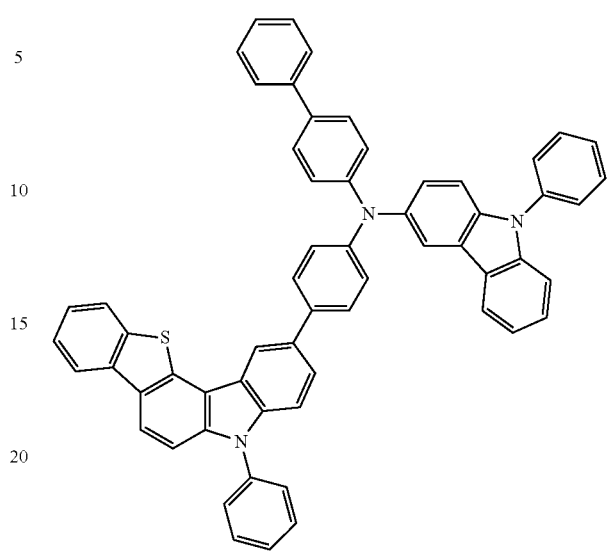
Compound 3-25
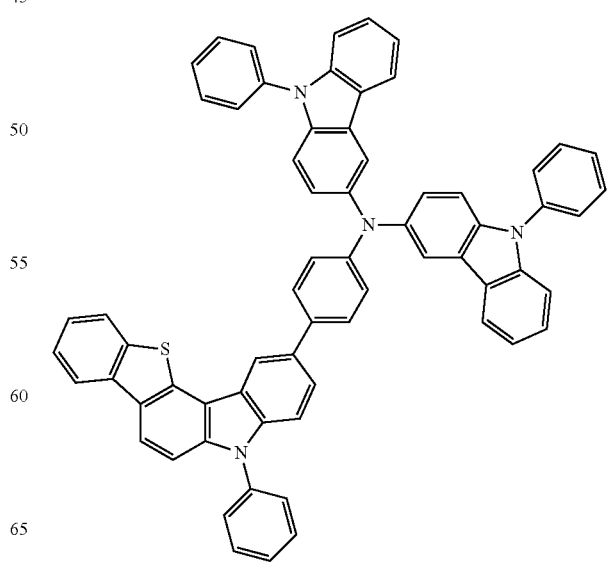

-continued
Compound 3-26
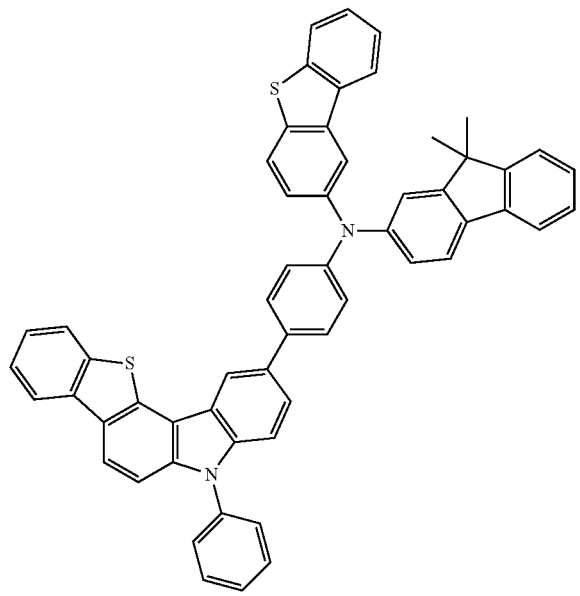
Compound 3-27
Compound 3-28
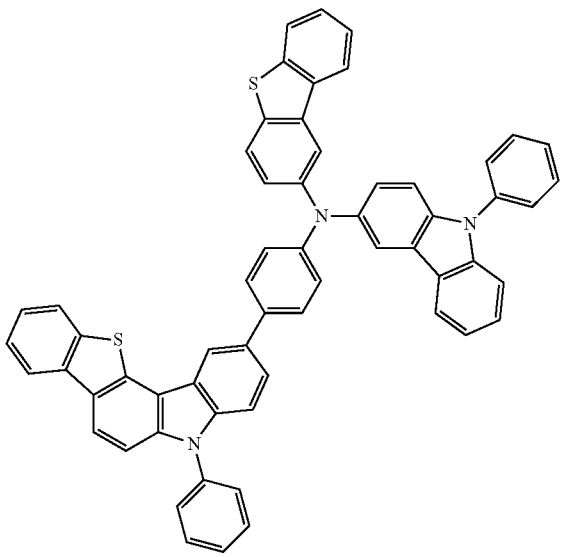
Compound 3-29

Compound 3-30
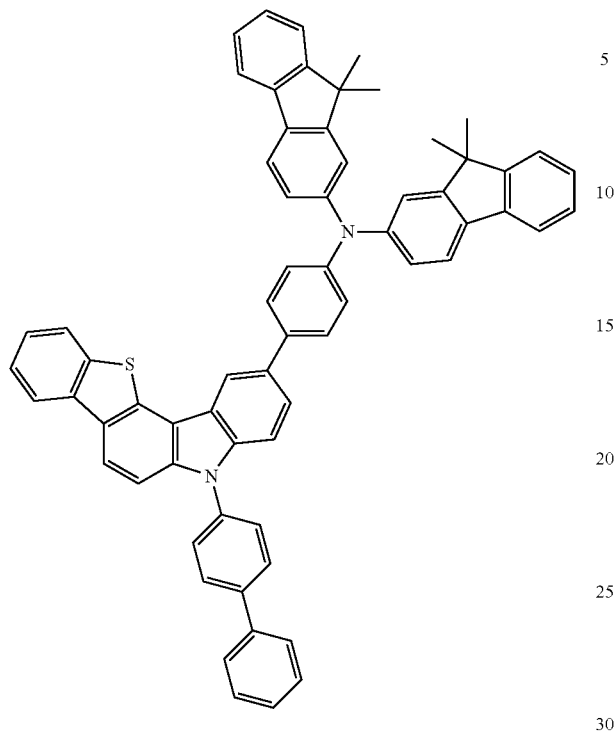
Compound 3-32
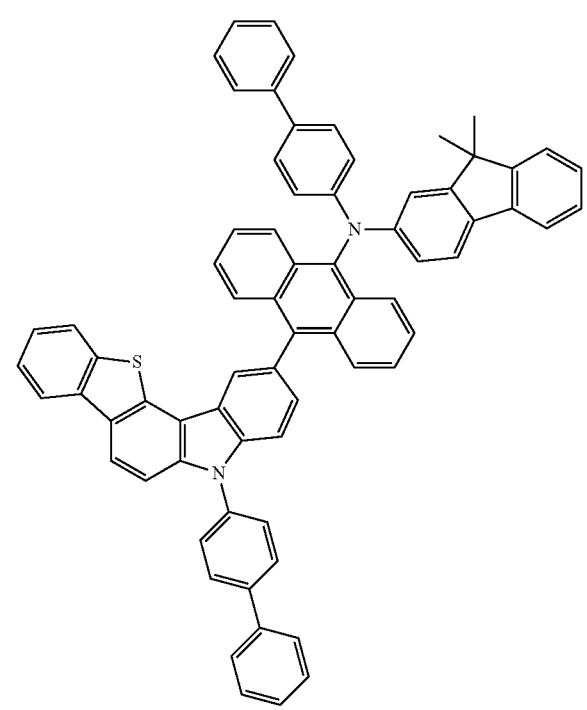
Compound 3-31
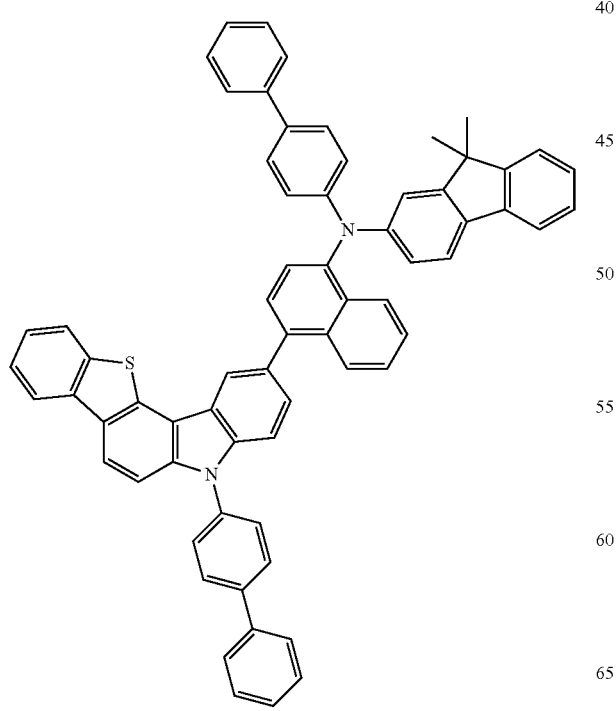
Compound 3-33
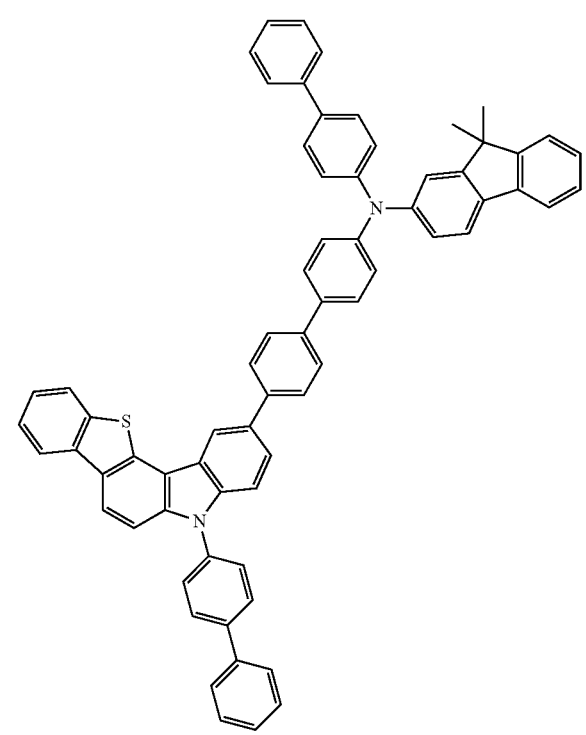

-continued
Compound 3-34
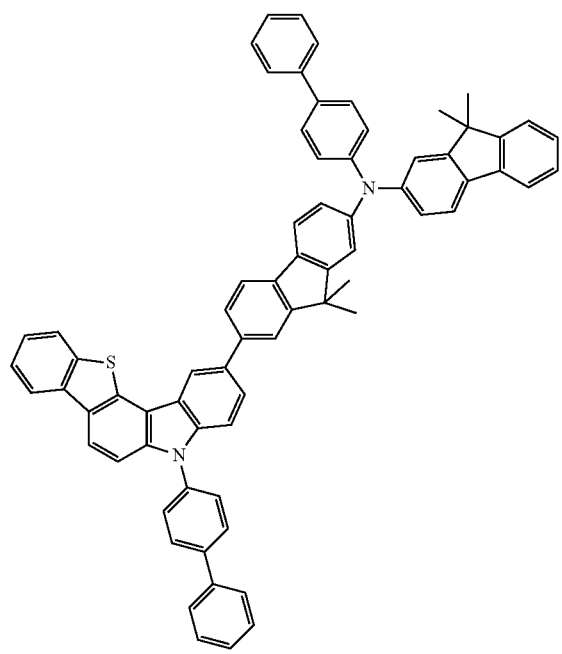
Compound 3-35
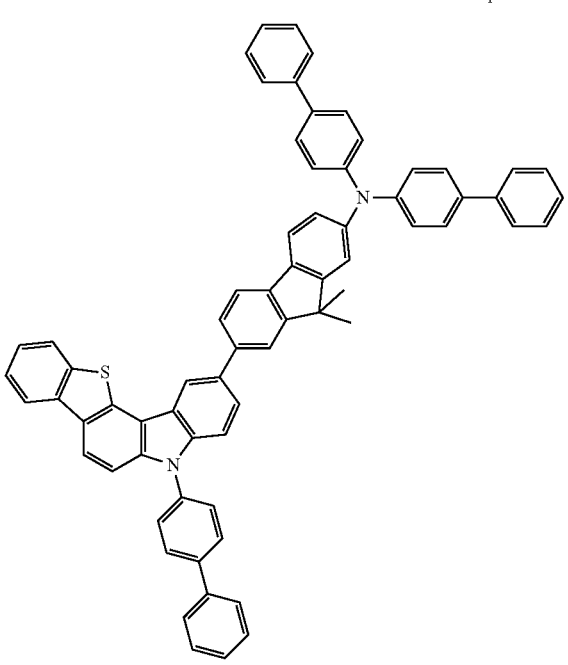
[Formula 11]
Compound 4-1
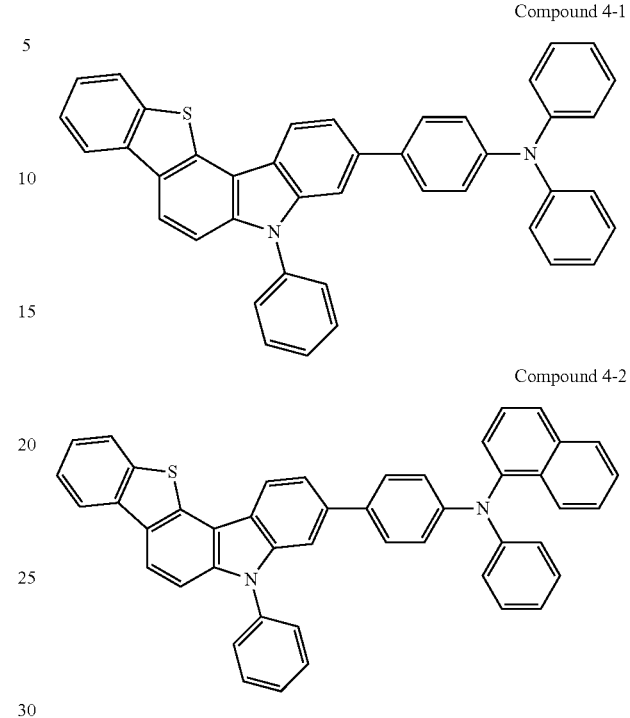
Compound 4-2
Compound 4-3
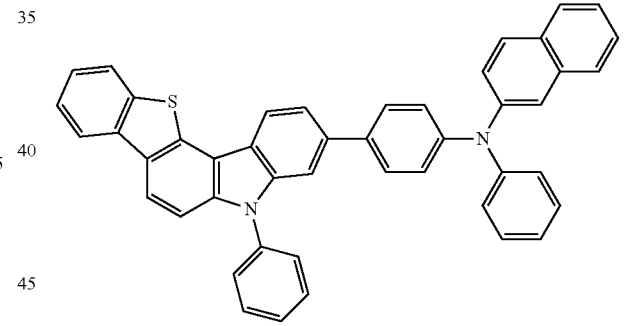
Compound 4-4
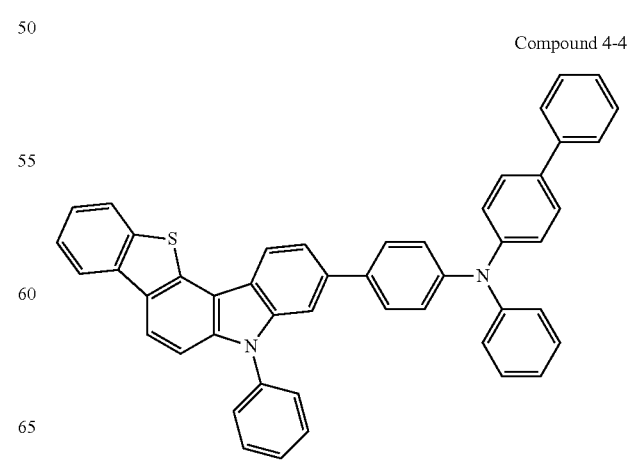

Compound 4-5
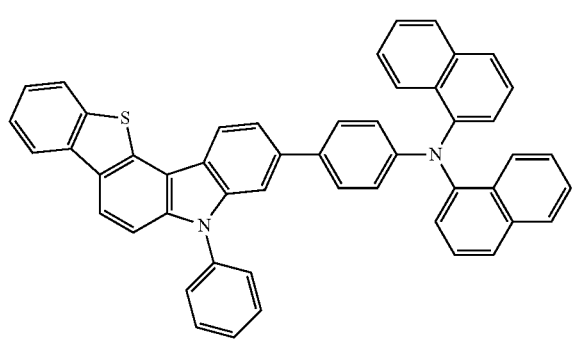
Compound 4-9
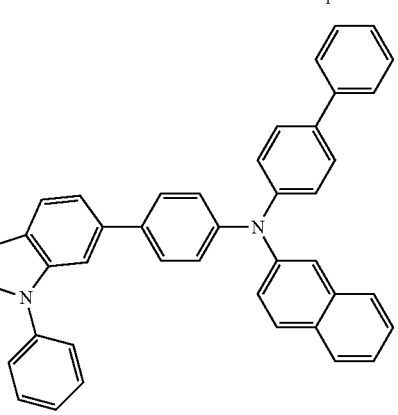
Compound 4-6
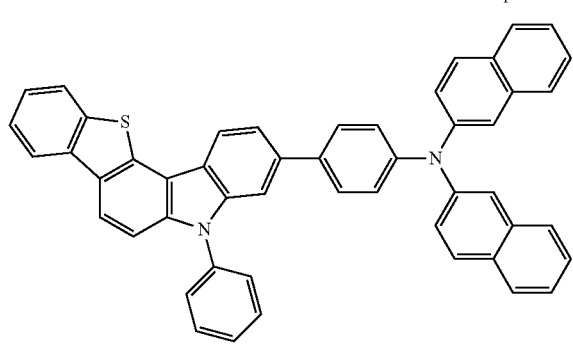
Compound 4-10
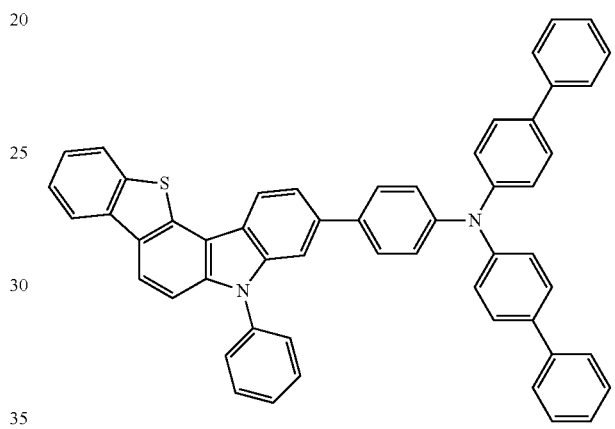
Compound 4-7
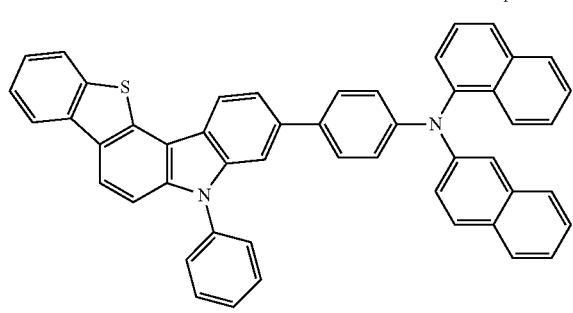
Compound 4-11
Compound 4-8
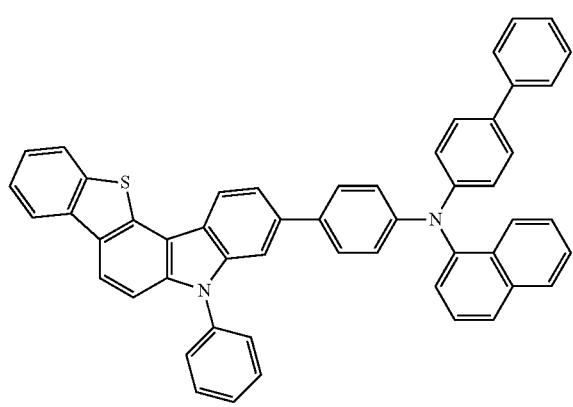
Compound 4-12
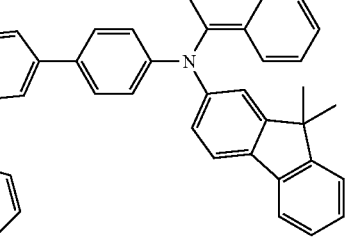

Compound 4-13
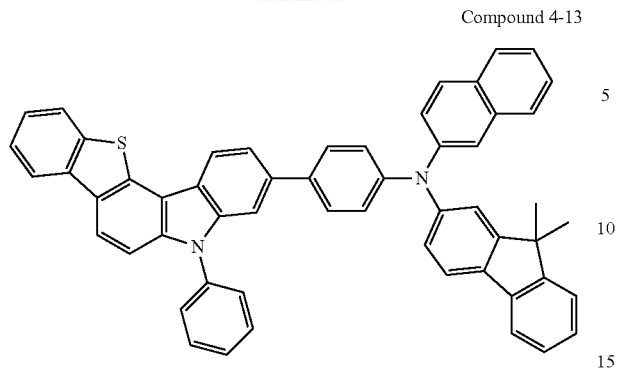
Compound 4-17
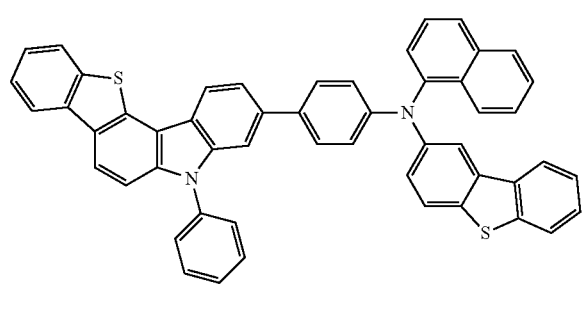
Compound 4-14
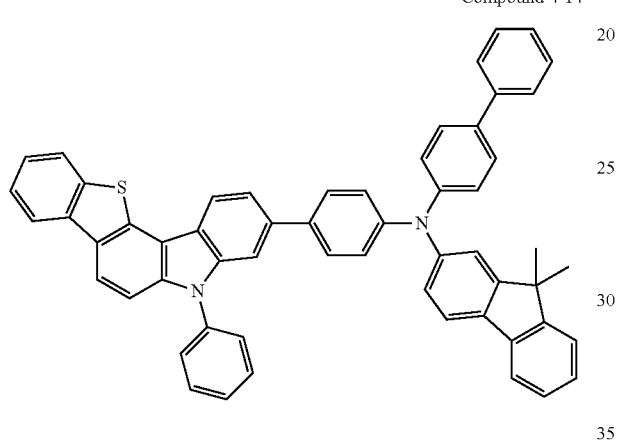
Compound 4-18
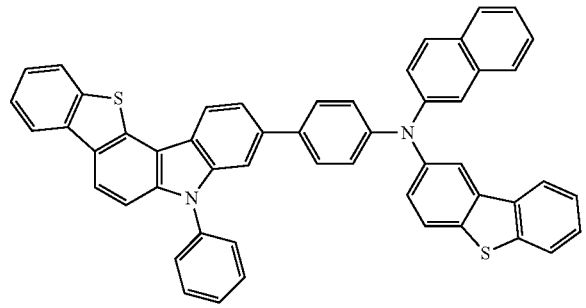
Compound 4-15
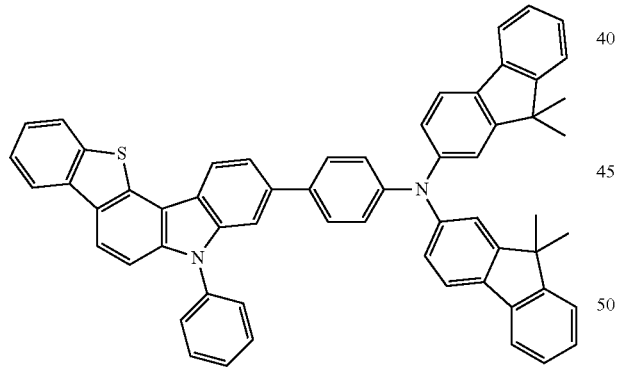
Compound 4-19
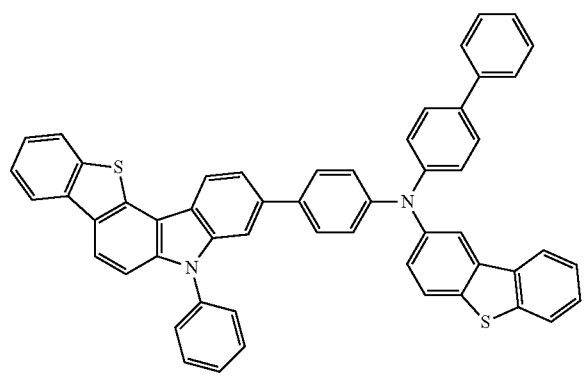
Compound 4-16
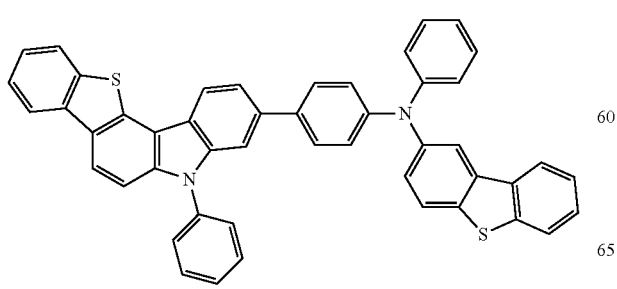
Compound 4-20
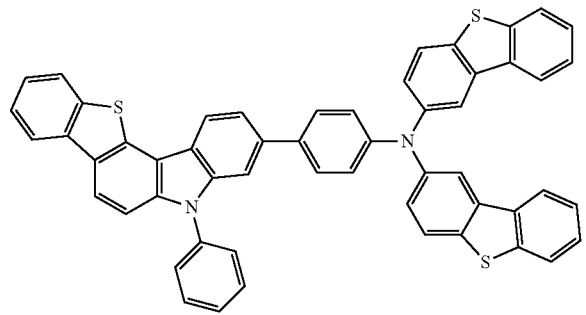

Compound 4-21
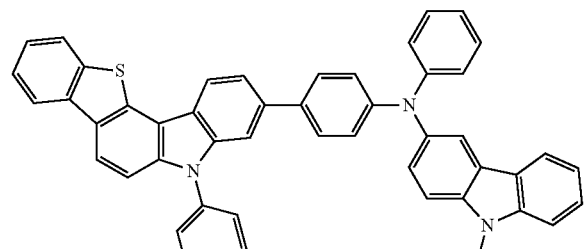
Compound 4-22
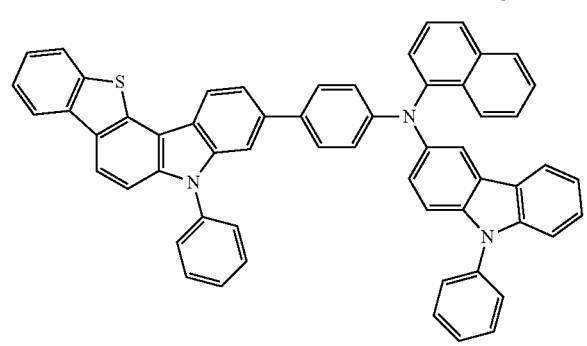
Compound 4-23
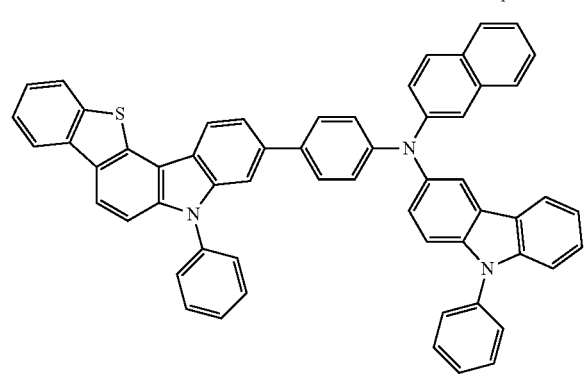
Compound 4-24
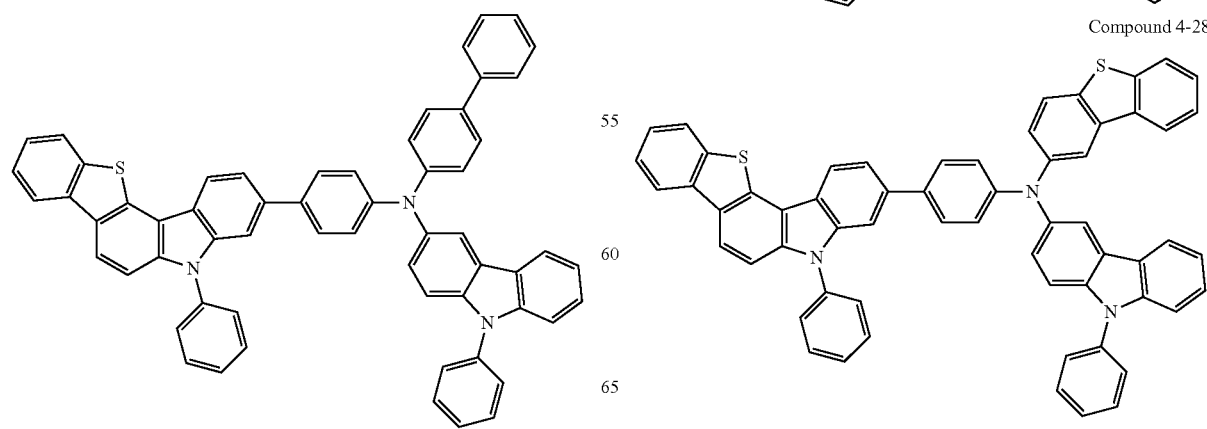
Compound 4-25
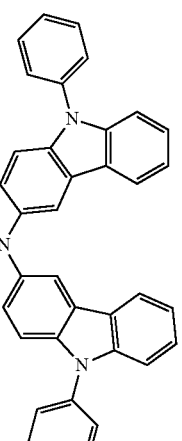
Compound 4-26
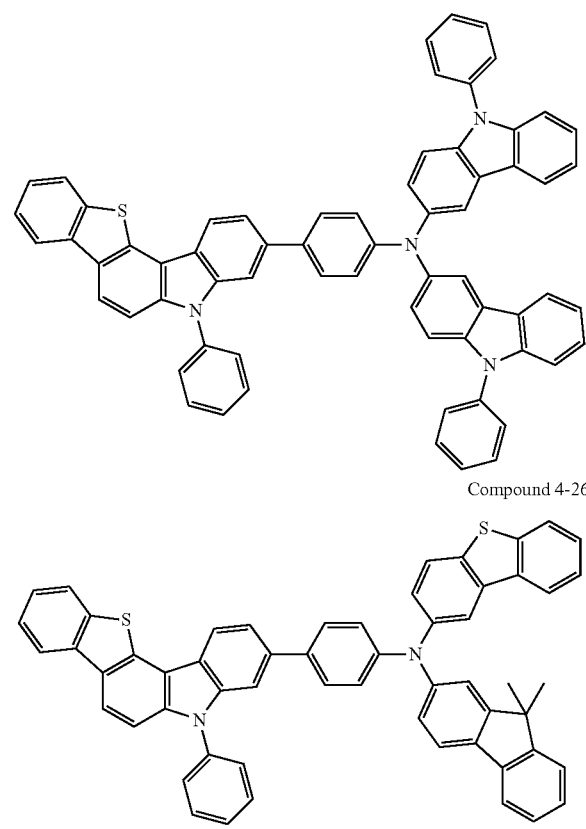
Compound 4-27
Compound 4-28
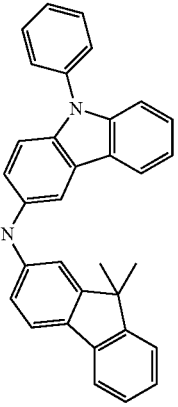

Compound 4-29
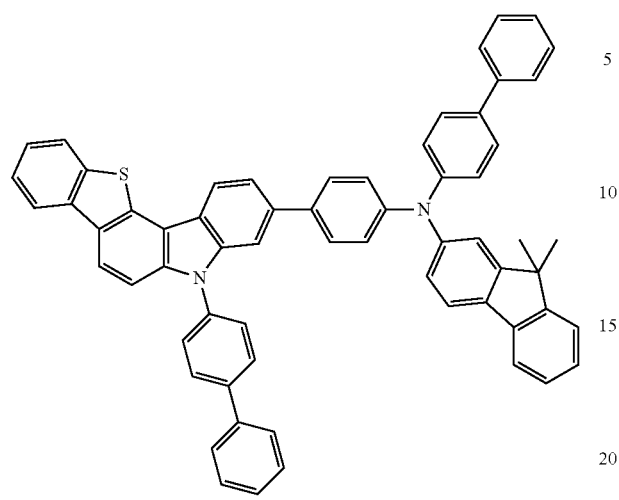
Compound 4-30
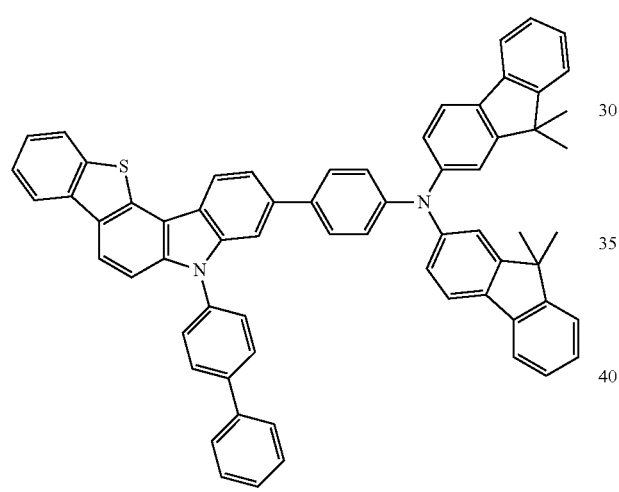
[Formula 12]
Compound 5-1
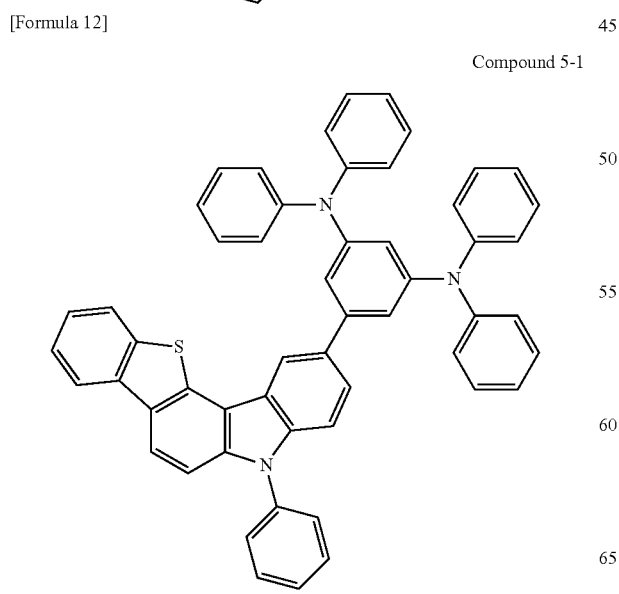
Compound 5-2
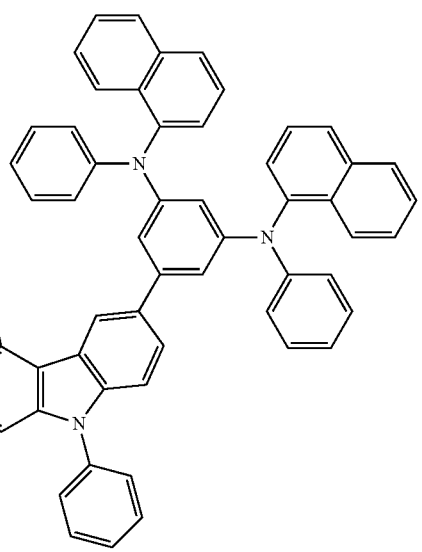
Compound 5-3
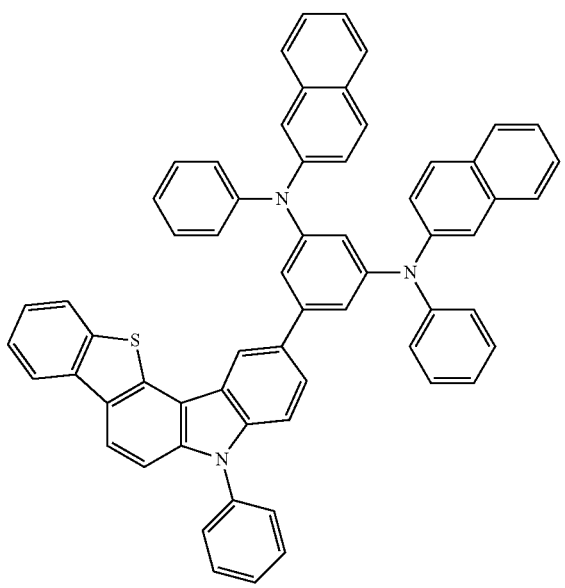

Compound 5-4
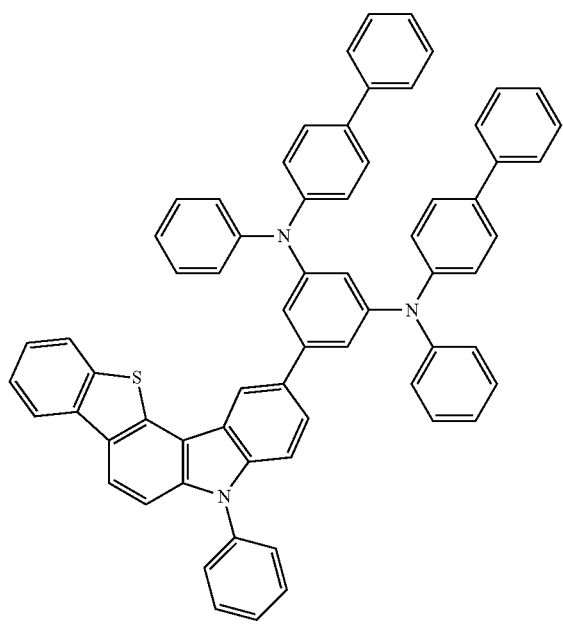
Compound 5-6
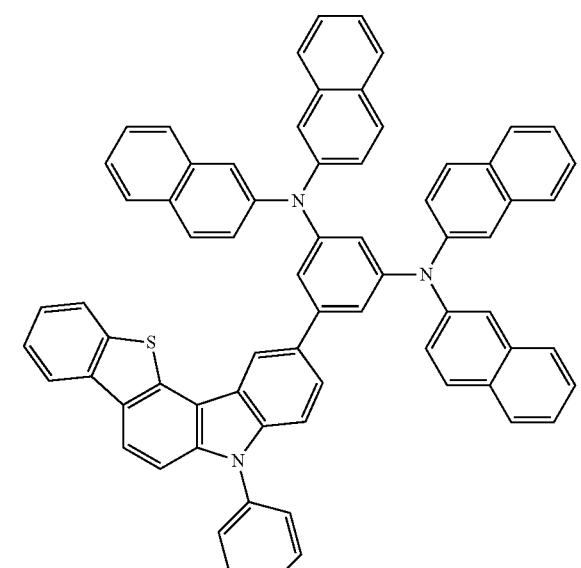
Compound 5-5
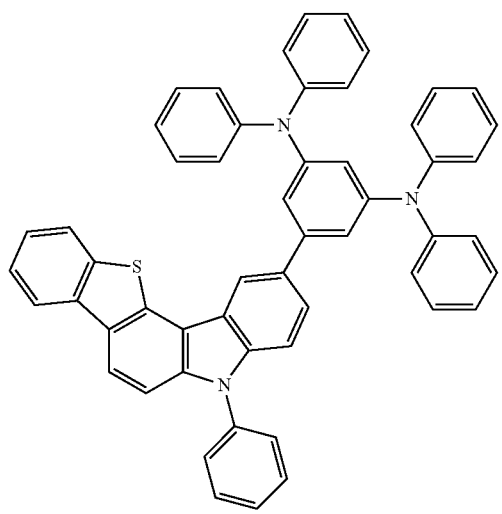
Compound 5-7
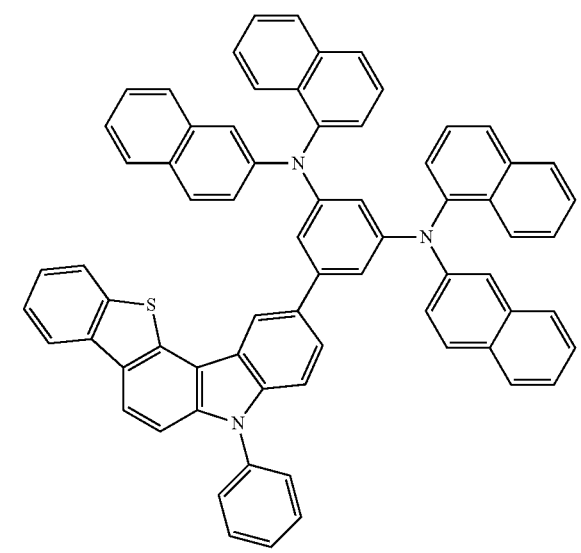

Compound 5-8
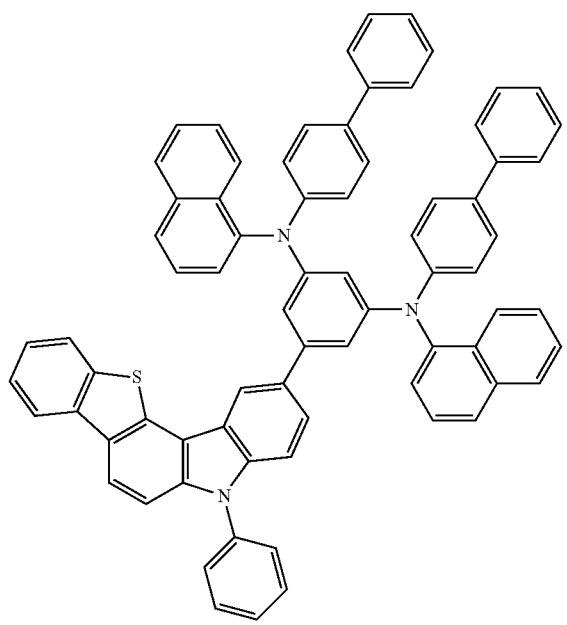
Compound 5-10
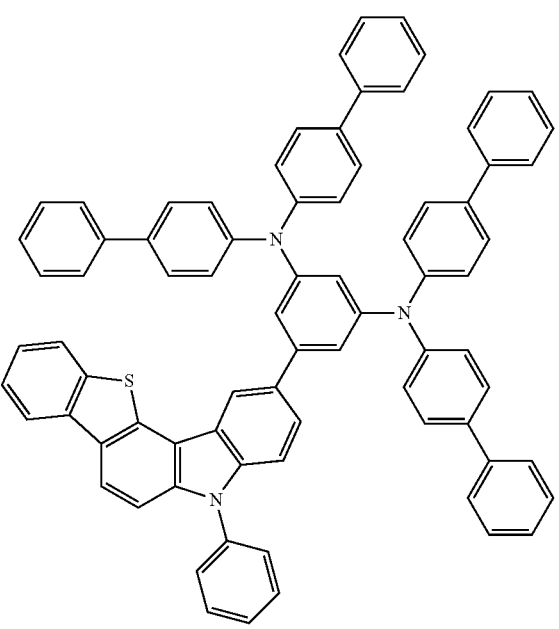
Compound 5-9
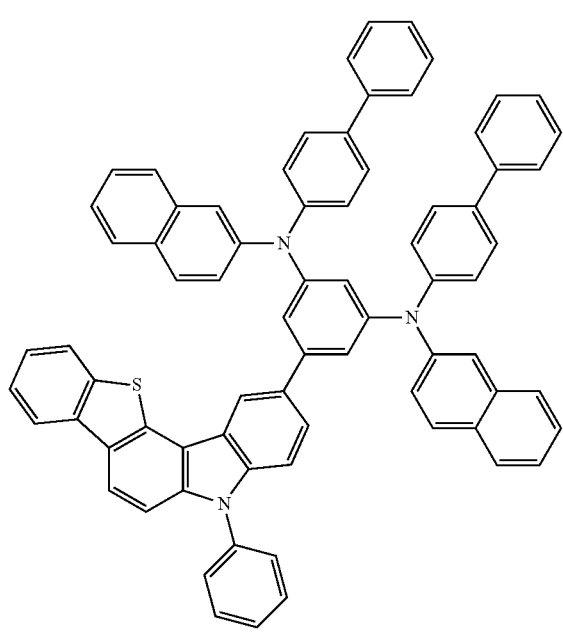
Compound 5-11
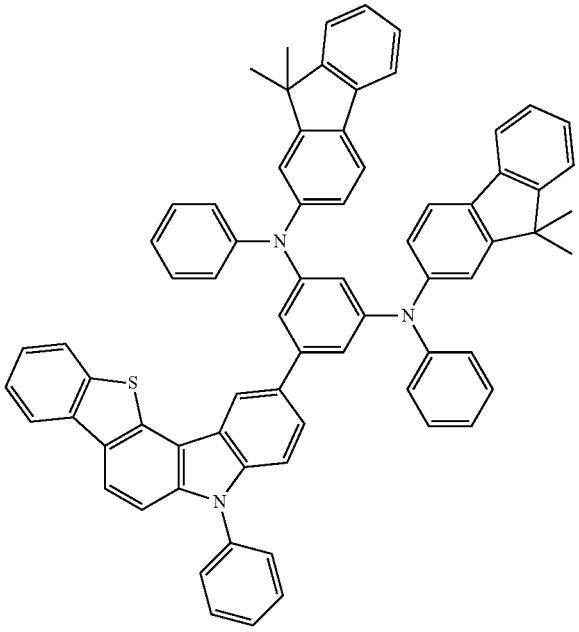

Compound 5-12
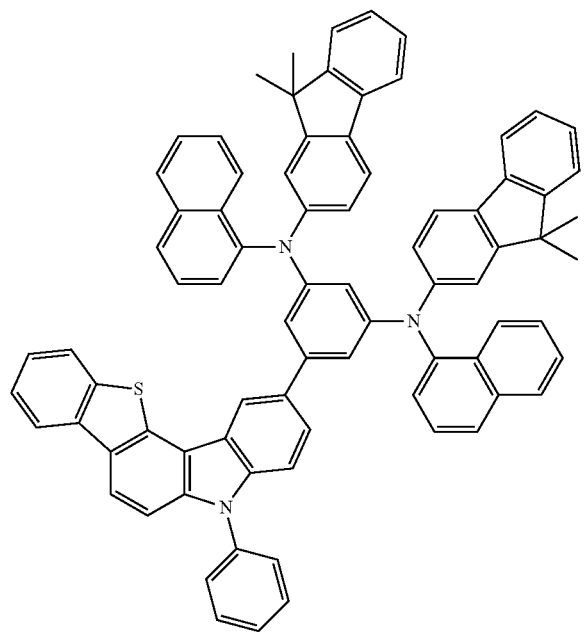
Compound 5-14
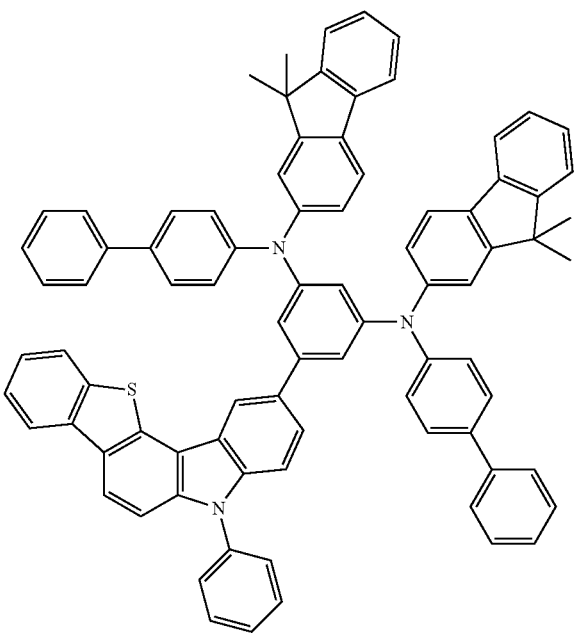
Compound 5-13
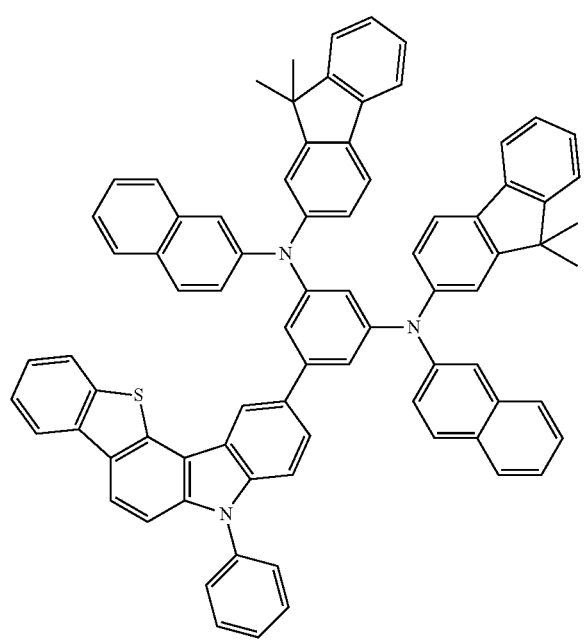
Compound 5-15
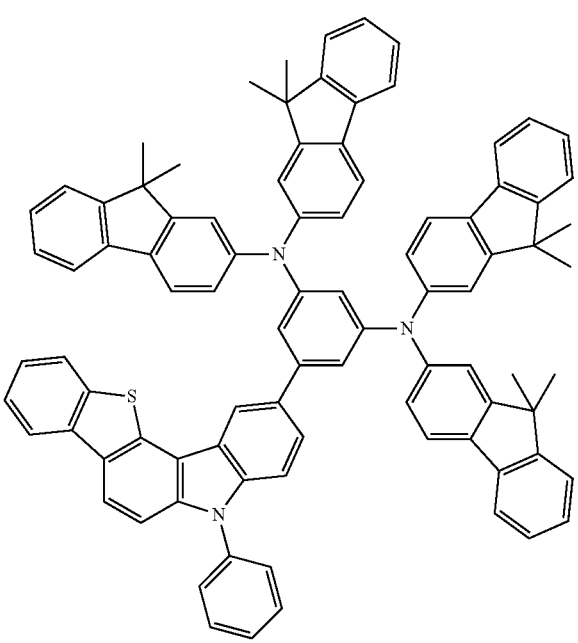

Compound 5-16
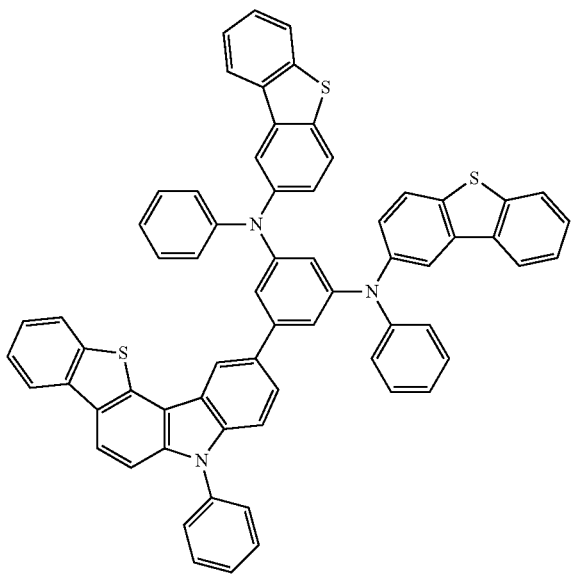
Compound 5-17
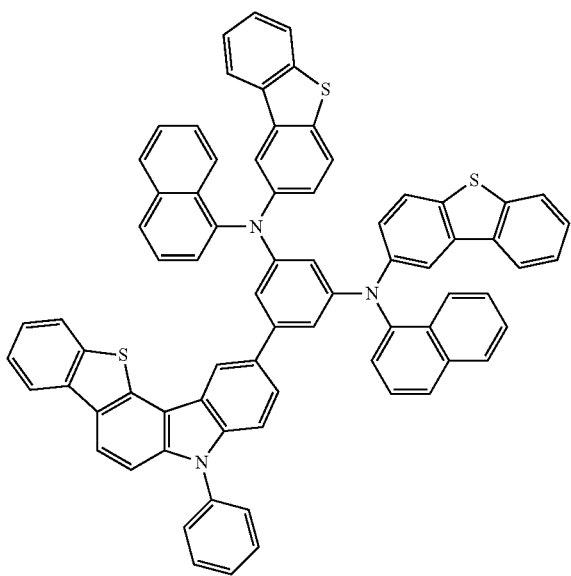
Compound 5-18
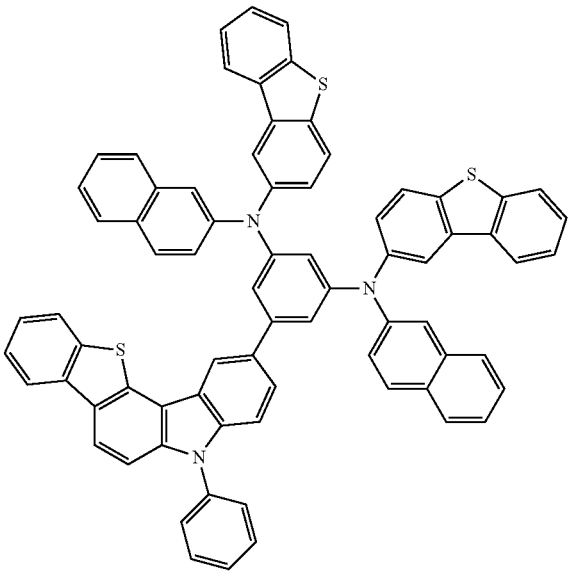
Compound 5-19
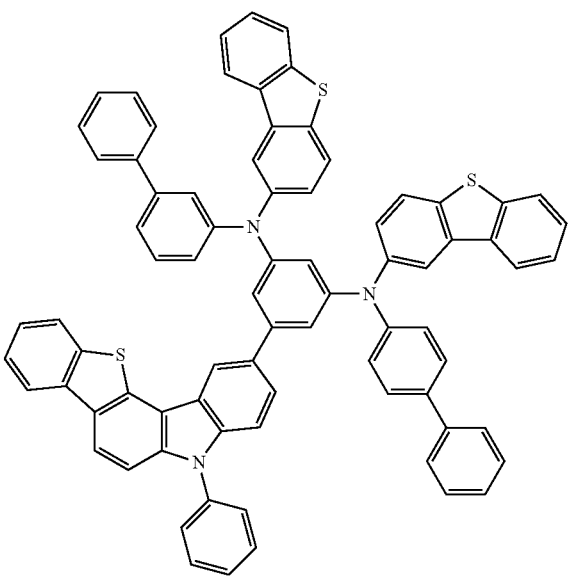

Compound 5-20
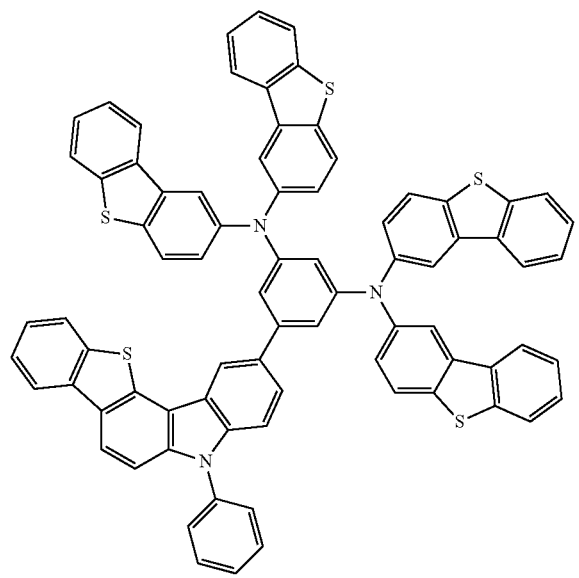
Compound 5-22
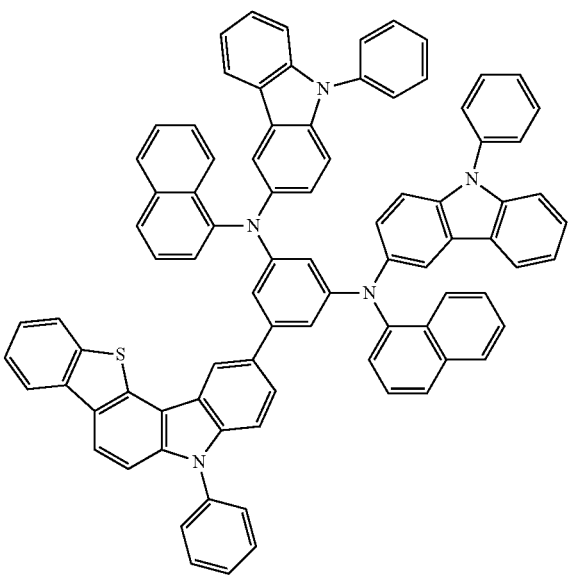
Compound 5-21
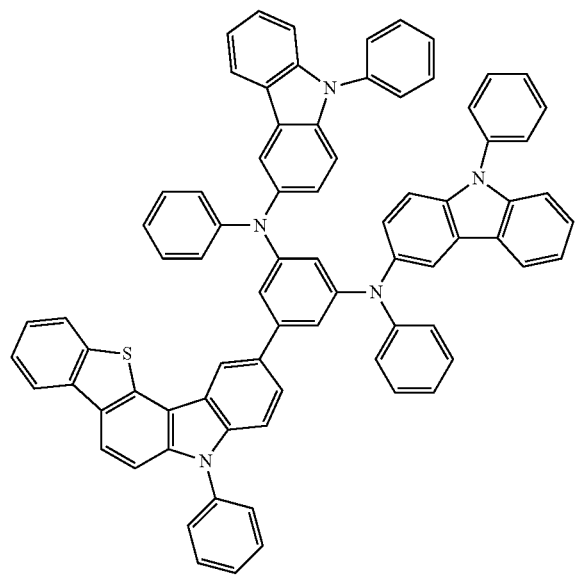
Compound 5-23
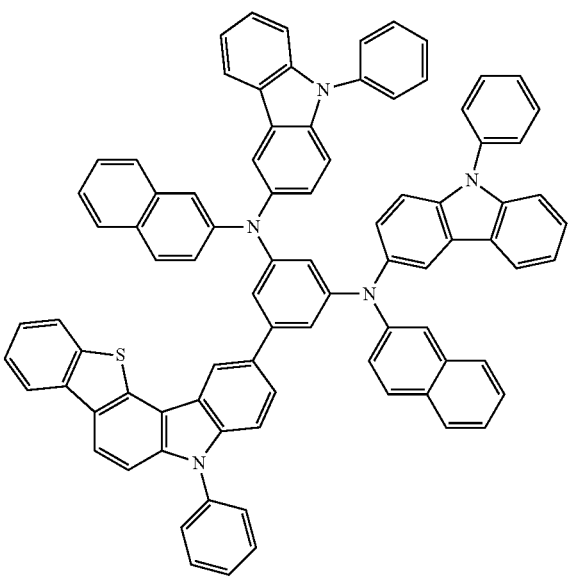

Compound 5-24
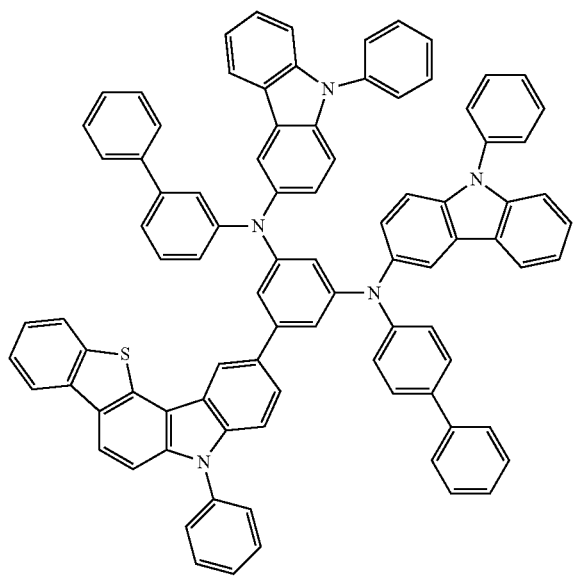
Compound 5-25
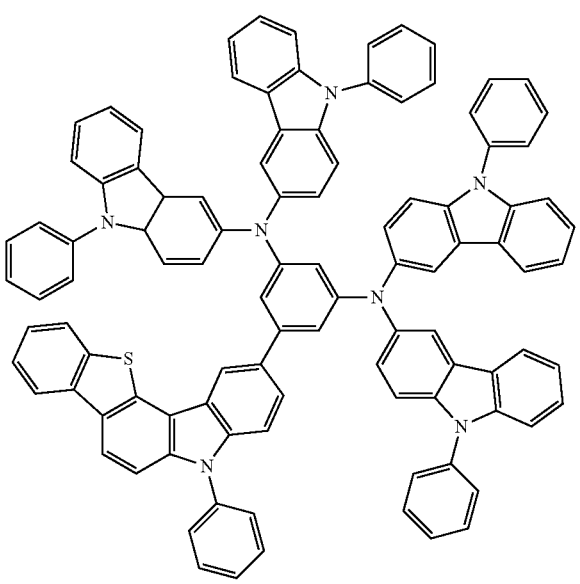
[Formula 13]
Compound 6-1
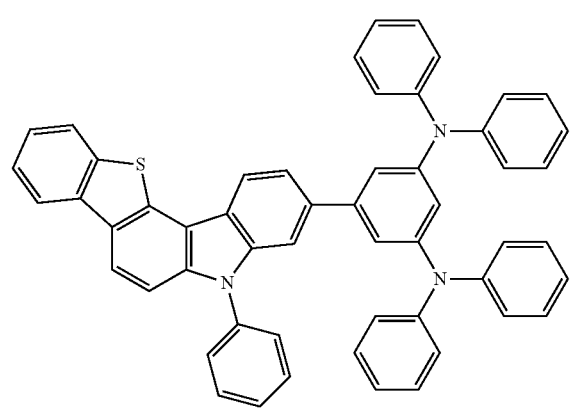
Compound 6-2
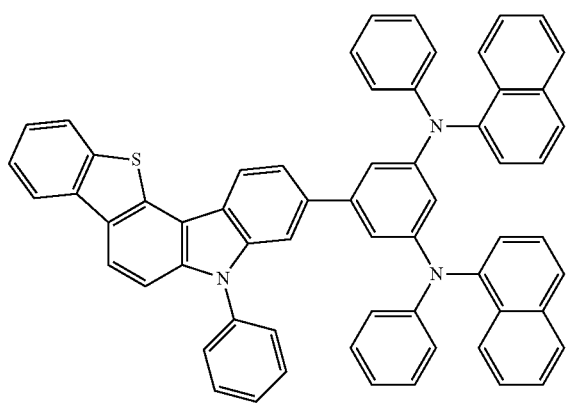
Compound 6-3
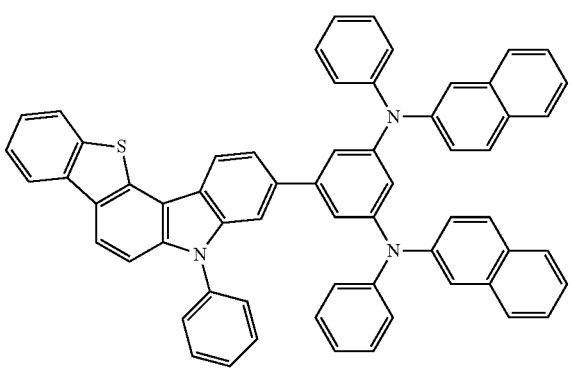
Compound 6-4
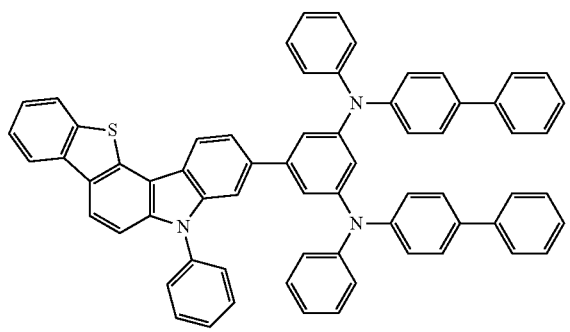
Compound 6-5
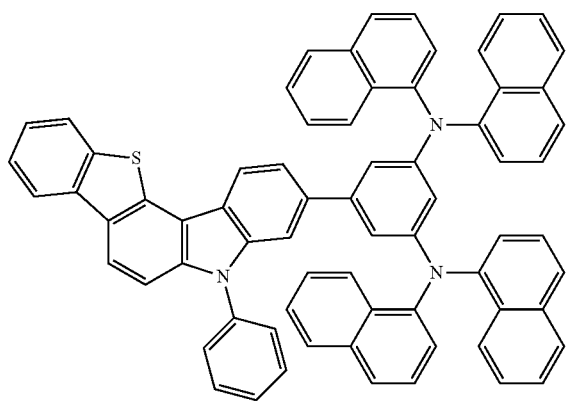

-continued
Compound 6-6
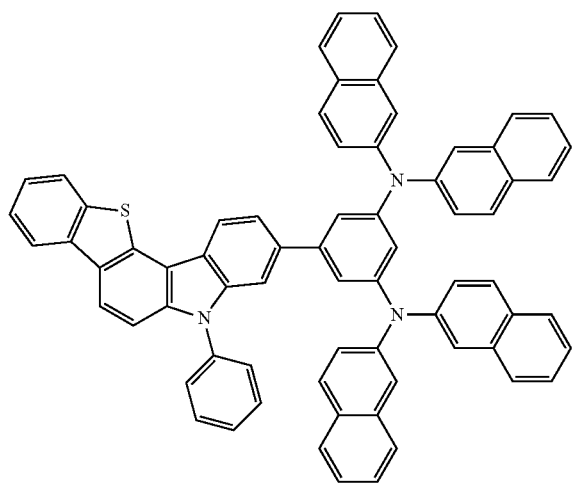
Compound 6-7
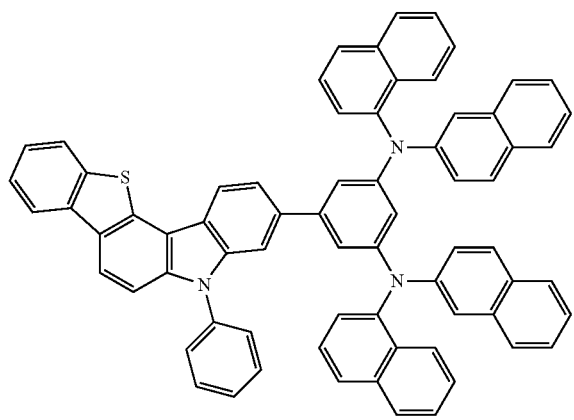
Compound 6-8
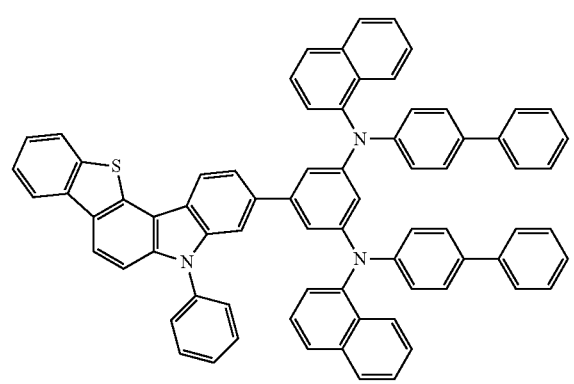
-continued
Compound 6-9
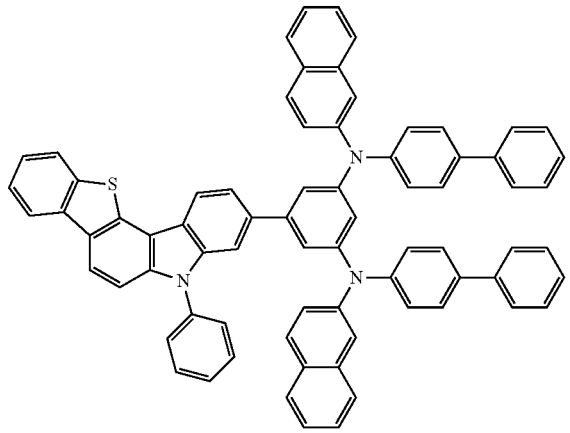
Compound 6-10
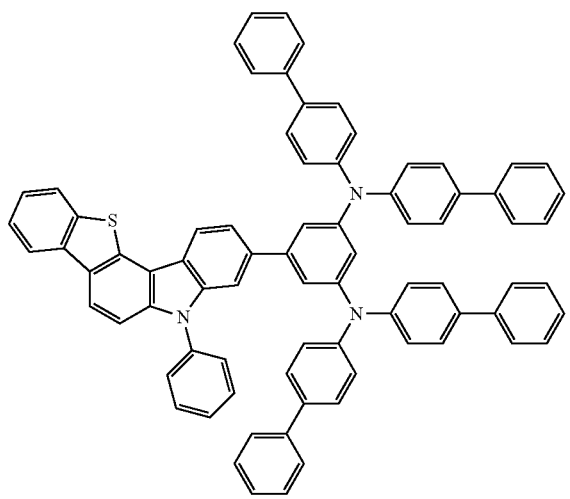
Compound 6-11
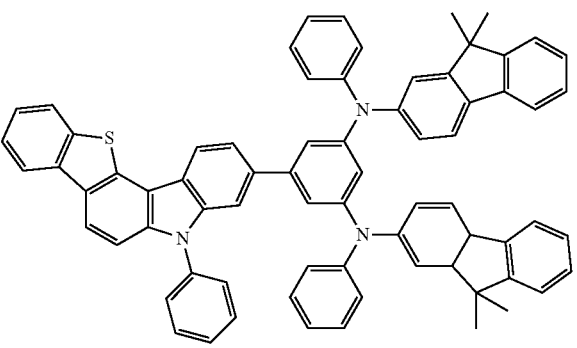

Compound 6-12
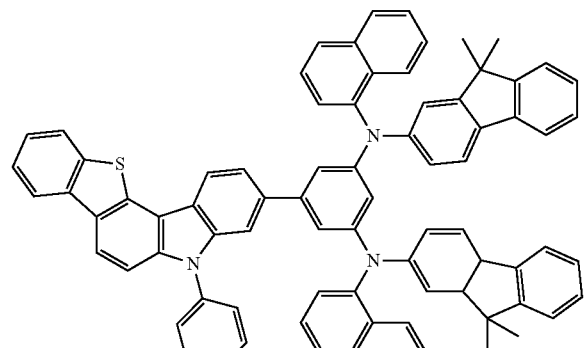
Compound 6-13
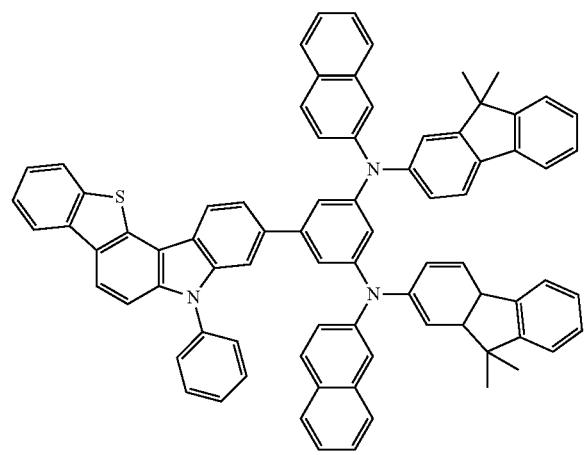
Compound 6-14
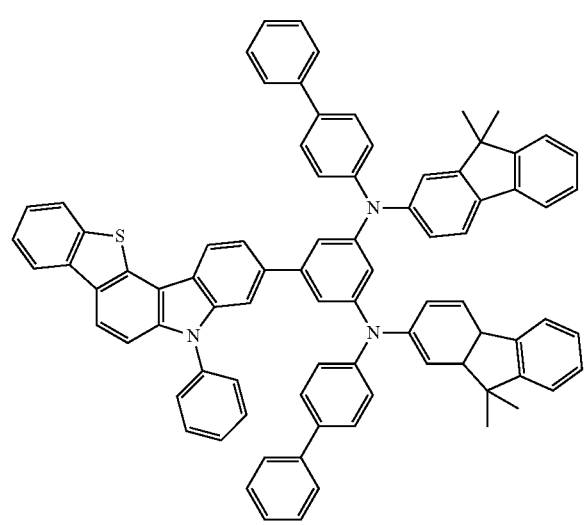
Compound 6-15
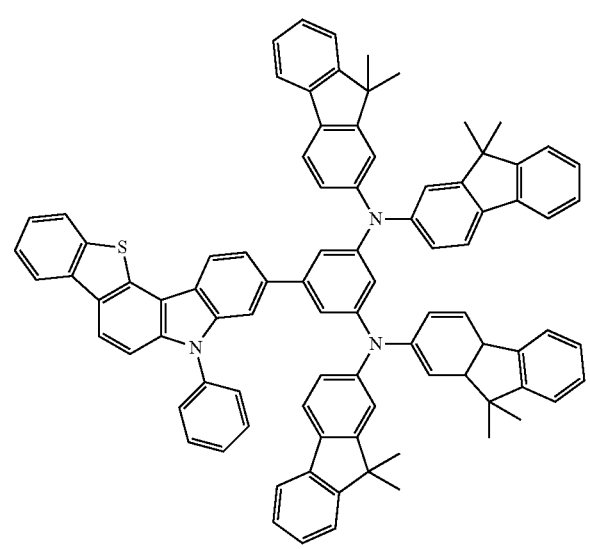
Compound 6-16
Compound 6-17
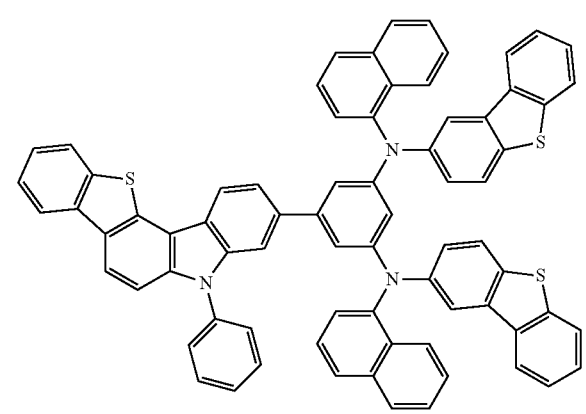

Compound 6-18
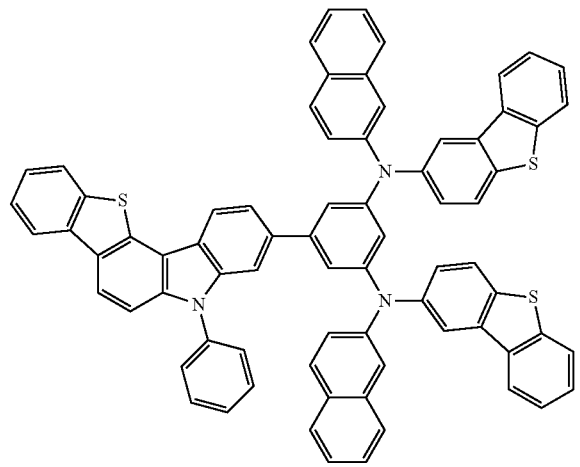
Compound 6-19
Compound 6-21
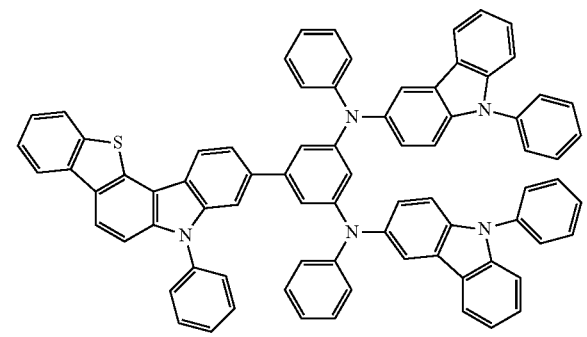
Compound 6-22
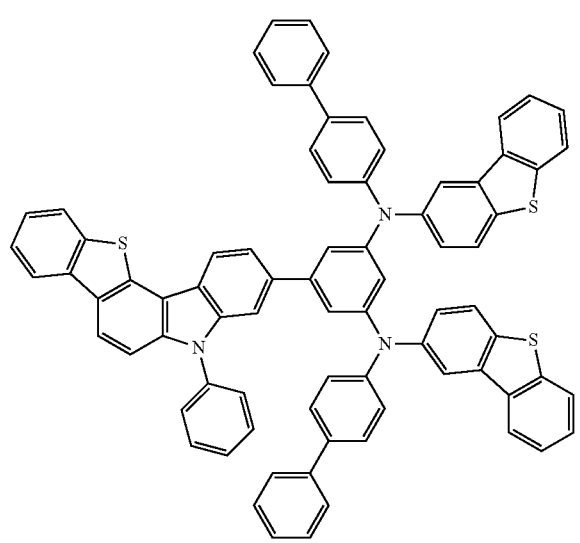
Compound 6-20
Compound 6-23
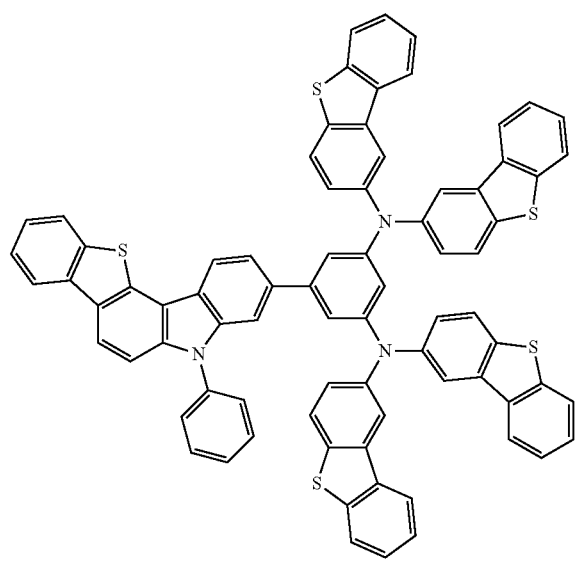

Compound 6-24

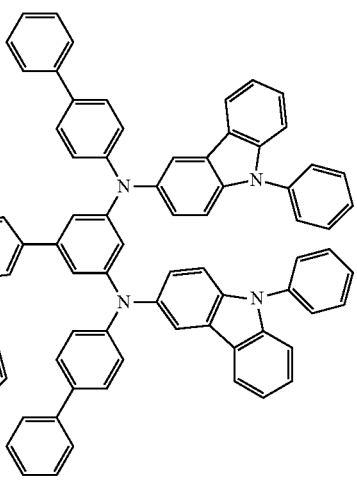

Compound 6-25

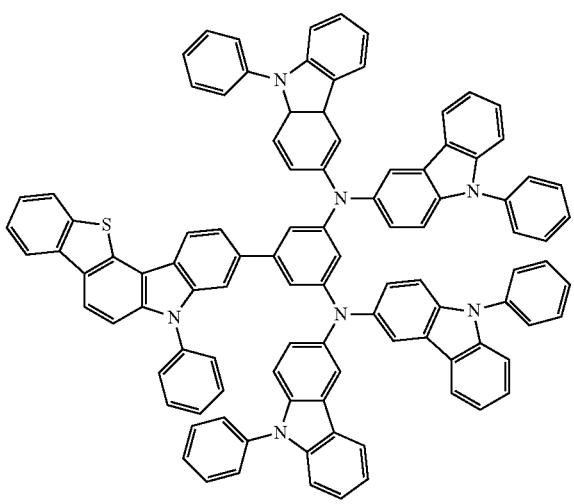

Compounds represented by Formulas 1 to 5 above each may be one of compounds represented by Formulas 6 to 13 above, but the present invention is not limited thereto. With regard to this, since there are a wide range of substituents for each of $R_1$ to $R_6$, X, Ar, Y, and Z of compounds represented by Formula 1, it is practically difficult to cover all compounds by Formulas 6 to 13. Thus, representative compounds are illustratively described, but other compounds represented by Formula 1, not presented in Formulas 6 to 13, may also form a part of this specification.

There are various organic electrical elements in which the five-membered heterocyclic compounds described with reference to Formulas 1 to 13 are used as an organic material layer. Examples of organic electrical elements to which the five-membered heterocyclic compounds described with reference to Formulas 1 to 13 are applicable may include an organic light emitting diode (OLED), an organic solar cell, an organic photo conductor (OPC) drum, an organic transistor (organic TFT), and the like.

As one example of the organic electrical elements in which the five-membered heterocyclic compounds described with reference to Formulas 1 to 13 may be employed, an organic light emitting diode (OLED) will be described below, but the present invention is not limited thereto, and the above described five-membered heterocyclic compounds may be employed in various organic electrical elements.

Another embodiment of the present invention provides an organic light emitting diode as an organic electrical element including a first electrode, a second electrode, and an organic material layer interposed between these electrodes, in which at least one of layers included in the organic material layer contains the compounds represented by Formulas 1 to 13.

Figure 2:
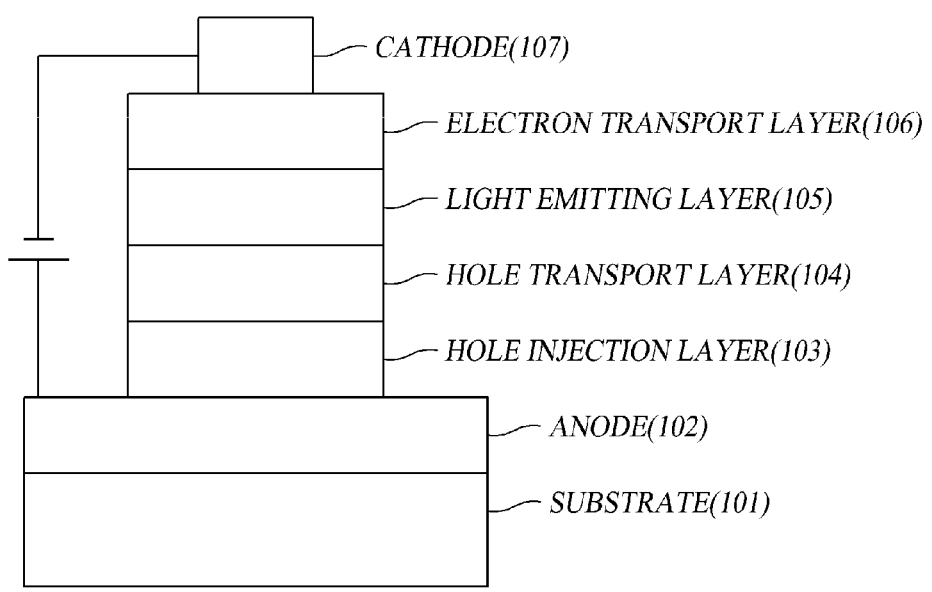
Figure 3:
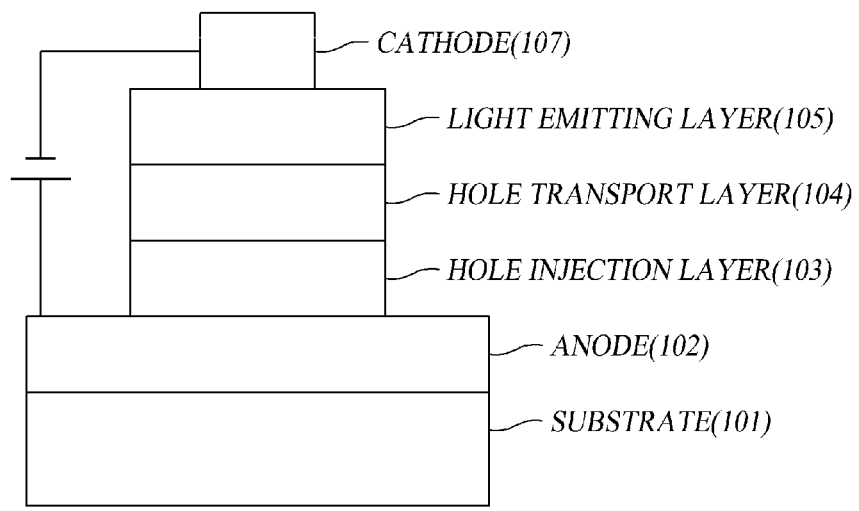
Figure 4:
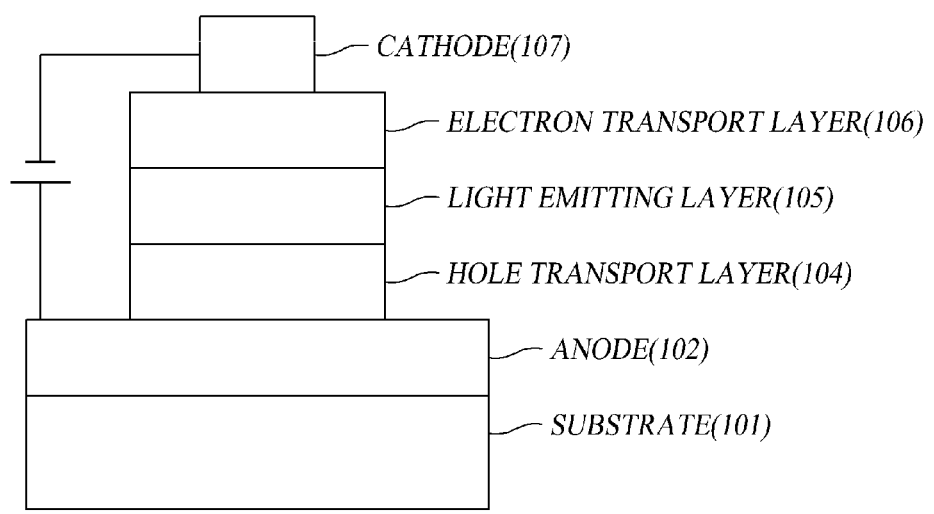
Figure 5:
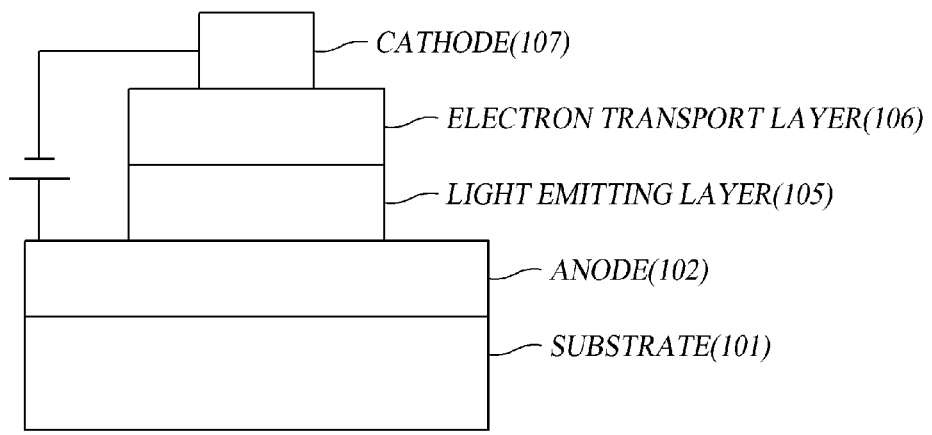
Figure 6:
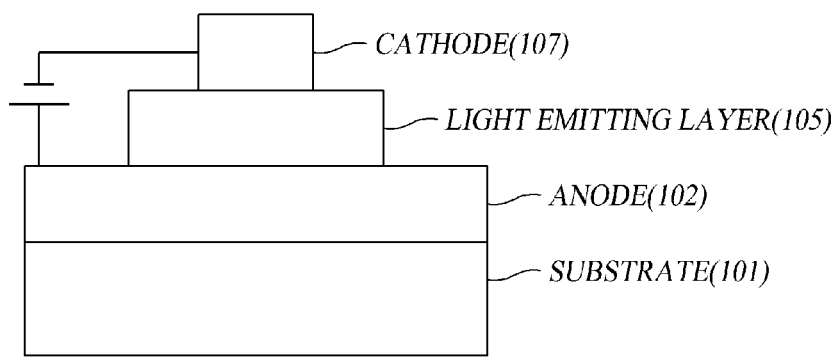

FIGS. 1 to 6 show examples of an organic light emitting diode in which a compound according to the present invention may be employed.

An organic light emitting diode according to another embodiment of the present invention may be manufactured by means of manufacturing methods and materials conventional in the art in such a manner as to have a structure known in the art, except that at least one of layers included in an organic material layer, including a hole injection layer, a hole transport layer, a light emitting layer, an electron transport layer, and an electron injection layer, is formed in such a manner as to contain the compounds represented by Formulas 1 to 13.

The structures of the organic light emitting diode according to another embodiment of the present invention are shown in FIGS. 1 to 6, but the present invention is not limited to these structures. In the example shown in FIG. 1, reference numeral "101" indicates a substrate, "102" indicates an anode, "103" indicates a hole injection layer (HIL), "104" indicates a hole transport layer (HTL), "105" indicates an emitting layer (EML), "106" indicates an electron injection layer (EIL), "107" indicates an electron transport layer (ETL), and "108" indicates a cathode. Although not shown, such an organic light emitting diode may further include a hole blocking layer (HBL) for blocking movement of holes, an electron blocking layer (EBL) for blocking movement of electrons, and a protective layer. The protective layer may be formed as an uppermost layer for protecting an organic material layer or a cathode.

With regard to this, the five-membered heterocyclic compound described with reference to Formulas 1 to 13 may be contained in at least one of layers included in an organic material layer, including a hole injection layer, a hole transport layer, an emitting layer, and an electron transport layer. More specifically, the five-membered heterocyclic compound described with reference to Formulas 1 to 13 may be substituted for at least one of a hole injection layer, a hole transport layer, an emitting layer, an electron transport layer, an electron injection layer, a hole blocking layer, an electron blocking layer, and a protective layer, or may be layered together with these layers. Of course, the compound may be used in not only one layer but also two or more layers of the organic material layers.

Especially, the five-membered heterocyclic compound described with reference to Formulas 1 to 13 may be used as a hole injection material, a hole transport material, an electron injection material, an electron transport material, a light emitting material, and a passivation (capping) material, and particularly, may be used alone as a light emitting material, a host, or a dopant.

For example, the organic light emitting diode according to another embodiment of the present invention may be manufactured by depositing a metal, a conductive metal oxide, or an alloy thereof on a substrate by means of PVD (physical vapor deposition) such as sputtering or e-beam evaporation to form an anode, forming an organic material layer including a hole injection layer, a hole transport layer, an emitting layer, an electron transport layer, and an electron injection layer thereon, and then depositing a material, which can be used as a cathode, thereon.

In addition to this method, an organic electrical element may be manufactured by sequentially depositing a cathode material, an organic material layer, and an anode material on a substrate. The organic material layer may be formed in a multi-layered structure including a hole injection layer, a hole transport layer, an emitting layer, an electron transport layer, an electron injection layer, and the like, but the present invention is not limited thereto, and the organic material layer may be formed in a single layer structure. Further, the organic material layer may be manufactured in such a manner that a smaller number of layers are formed using various polymer materials by means of a solvent process, for example, spin coating, dip coating, doctor blading, screen printing, inkjet printing, or thermal transfer instead of deposition.

In the organic light emitting diode according to another embodiment of the present invention, the above described five-membered heterocyclic compound may be used in a soluble process such as a spin coating process or an ink jet process.

A substrate is a support for the organic light emitting diode, and a silicon wafer, a quartz or glass plate, a metal plate, a plastic film or sheet, and the like may be used as the substrate.

An anode is disposed on the substrate. This anode injects holes into a hole injection layer disposed thereon. Preferably, a material having a high work function is used as an anode material so that injection of holes into an organic material layer can be smoothly achieved. Specific examples of an anode material that may be used in the present invention may include: metals such as vanadium, chromium, copper, zinc, and gold, or alloys thereof; metal oxides such as zinc oxide, indium oxide, indium tin oxide (ITO), and indium zinc oxide (IZO); a metal-oxide combination such as ZnO:Al or $SnO_2$:Sb; and conductive polymers such as poly(3-methylthiophene), poly[3,4-(ethylene-1,2-dioxy)thiophene] (PEDT), polypyrrole, and polyaniline, but the present invention is not limited thereto.

A hole injection layer is disposed on the anode. A material for this hole injection layer is required to have a high efficiency for injecting holes from an anode and have the ability to efficiently transport the injected holes. To this end, the material must have a low ionization potential, a high transparency to visible rays, and a high stability for holes.

A material suitable for use as a hole injection material is a material into which holes can be readily injected from an anode at a low voltage, and the HOMO (highest occupied molecular orbital) of the hole injection material preferably ranges between a work function of an anode material and the HOMO of an adjacent organic material layer. Specific examples of the hole injection material may include metal porphyrine-, oligothiophene-, and arylamine-based organic materials, hexanitrile hexaazatriphenylene- and quinacridone-based organic materials, a perylene-based organic material, and anthraquinone-, polyaniline-, and polythiophene-based conductive polymers, but the present invention is not limited thereto.

A hole transport layer is disposed on the hole injection layer. This hole transport layer serves to receive holes transferred from the hole injection layer and transfer them to an organic emitting layer disposed thereon. Further, the hole transport layer has high hole mobility and high stability for holes and also plays a role of blocking electrons. In addition to these general requirements, the hole transport layer requires heat-resistance for an element when being applied to a vehicle display, and thus is preferably made of a material having a glass transition temperature (Tg) of 70° C. or more. The examples of a material satisfying these requirements may include NPD (also referred to as NPB), a spiro-arylamine-based compound, a perylene-arylamine-based compound, an azacycloheptatriene compound, bis(diphenylvinylphenyl) anthracene, a silicon-germanium oxide compound, a silicon-based arylamine compound, and the like.

An organic emitting layer is disposed on the hole transport layer. This organic emitting layer refers to a layer in which holes and electrons injected from an anode and a cathode respectively are recombined to emit light, and is made of a material having high quantum efficiency. A material suitable for use as a light emitting material is a material that combines holes and electrons transferred from a hole transport layer and an electron transport layer respectively and thereby emits light in a visible ray range. Preferably, a material having high quantum efficiency for fluorescence or phosphorescence may be used.

As a material or a compound satisfying these requirements, for green light emission, Alq3 may be used, and for blue light emission, Balq (8-hydroxyquinoline beryllium salt), a DPVBi (4,4'-bis(2,2-diphenylethenyl)-1,1'-biphenyl) based material, a Spiro material, spiro-DPVBi (Spiro-4,4'-bis(2,2-diphenylethenyl)-1,1'-biphenyl), LiPBO (2-(2-benzoxazoyl)-phenol lithium salt), bis(diphenylvinylphenylvinyl) benzene, an aluminum-quinoline metal complex, metal complexes of imidazole, thiazole, and oxazole, or the like may be used. In order to improve blue light emission efficiency, a blue light emitting material may be doped with a small amount of perylene and BczVBi (3,3'[(1,1'-biphenyl)-4,4'-diyldi-2,1-ethenediyl]bis(9-ethyl)-9H-carbazole; DSA (distrylamine)). For red light emission, a green light emitting material doped with a small amount of DCJTB ([2-(1,1-dimethylethyl)-6-[2-(2,3,6,7-tetrahydro-1,1,7,7-tetramethyl-1H,5H-benzo(ij)quinolizin-9-yl)ethenyl]-4H-pyran-4-ylidene]-propanedinitrile) may be used. When an emitting layer is formed by means of a process such as inkjet printing, roll coating, spin coating, or the like, a polymer such as a polyphenylenevinylene (PPV)-based polymer or poly fluorene may be used for an organic emitting layer.

An electron transport layer is disposed on the organic emitting layer. This electron transport layer requires a material that has high efficiency for electrons injection from a cathode disposed thereon and can efficiently transport the injected electrons. To this end, the electron transport layer must be made of a material having high electron affinity, high electron mobility, and high stability to electrons. Specific examples of an electron transport material satisfying these requirements may include an Al complex of 8-hydroxyquinoline; a complex containing $Alg_a$; an organic radical compound; and a hydroxyflavone-metal complex, but the present invention is not limited thereto.

An electron injection layer is laminated on the electron transport layer. The electron injection layer may be manufactured using a low molecular weight material containing a metal complex compound (such as Balq, Alq3, Be(bq)2, Zn(BTZ)2, Zn(phq)2, PBD, spiro-PBD, TPBI, and Tf-6P), an aromatic compound having an imidazole ring, or a boron compound. Here, the electron injection layer may be formed in a thickness range of 100 Å to 300 Å.

A cathode is disposed on the electron injection layer. This cathode serves to inject electrons. The same material as that used for the anode is possibly used as a material for the cathode. For efficient electron injection, a metal having a low work function is more preferably used. Especially, an appropriate metal such as tin, magnesium, indium, calcium, sodium, lithium, aluminum, silver, or an alloy thereof may be used. Further, an electrode with a double-layer structure, such as lithium fluoride and aluminum, lithium oxide and aluminum, and strontium oxide and aluminum, may be used with a thickness of 100 µm or less.

According to used materials, the organic light emitting diode according to the present invention may be of a top emission type, a bottom emission type, or a dual emission type.

In addition, the present invention provides a terminal including a display device, which includes the above described organic electrical element, and a control unit for driving the display device. The terminal means a wired/wireless communication terminal which is currently used or will be used in the future. The inventive terminal as described above may be a mobile communication terminal such as a cellular phone, and may include all kinds of terminals such as a PDA, an electronic dictionary, a PMP, a remote controller, a navigation unit, a game player, various kinds of TVs, and various kinds of computers.

EXAMPLE

Hereinafter, the present invention will be described in more detail through Preparation Examples and Test Examples. However, the following examples are only for illustrative purposes and are not intended to limit the scope of the invention.

Preparation Example

Hereinafter, Preparation Examples or Synthesis Examples of the five-membered heterocyclic compounds presented in Formulas 8 to 13 will be described. However, since there are a number of five-membered heterocyclic compounds belonging to Formula 1, some of them will be selectively described by way of example. It will be apparent to those skilled in the art that other five-membered heterocyclic compounds according to the present invention can be prepared through Preparation Examples as described below although they are not exemplified herein.

Synthesis Method

1. Synthesis Method of Compound 1-15

[Reaction Scheme 1]

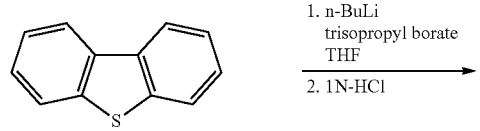

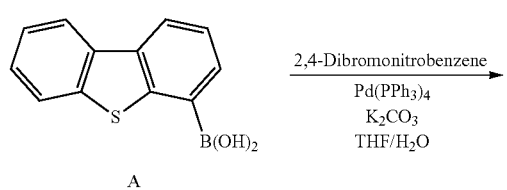

A

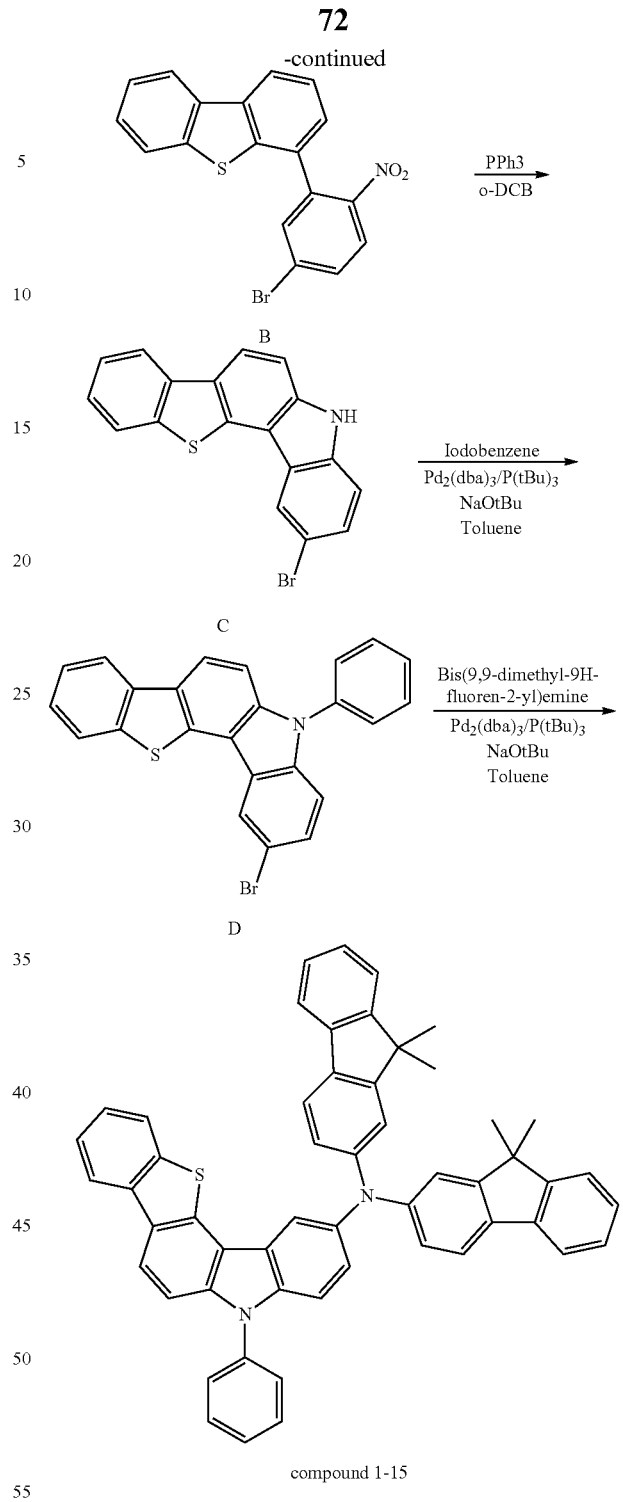

With reference to Reaction Scheme 1 above, preparation methods of intermediates A to D and a preparation method of compound 1-15 will be described below.

Synthesis of Intermediate A

Dibenzothiophene was dissolved in anhydrous tetrahydrofurane (THF), and the temperature of the reactants was lowered to −78° C. n-BuLi (2.5 M in hexane) was slowly added dropwise to the reactants, and then the reactants were stirred for 1 hour at 0° C. Subsequently, the temperature of the reactants was lowered to −78° C., and a triisopropyl borate solution dissolved in tetrahydrofuran (THF) was added dropwise to the reactants, followed by stirring for 12 hours at room temperature. Upon completion of the reaction, the reaction product was added with 1N—HCl aqueous solution, stirred for 30 minutes, and then extracted with ether. A small amount of water was removed from the extract by anhydrous magnesium sulfate (MgSO$_4$), the extract was subjected to vacuum-filtration, and then the filtrated organic solvent was concentrated. The resultant product was separated by column chromatography, with the result that desired intermediate A was obtained with a yield of 71%.

Synthesis of Intermediate B

The intermediate A obtained from the above step, 2,4-dibromonitrobenzene, Pd(PPh$_3$)$_4$, and potassium carbonate (K$_2$CO$_3$) were dissolved in tetrahydrofuran (THF) and a small amount of water, followed by reflux for 24 hours. Upon completion of the reaction, the reaction product was cooled to room temperature, extracted with dichloromethane (CH$_2$Cl$_2$), and washed with water. A small amount of water was removed from the extract by anhydrous magnesium sulfate (MgSO$_4$), the extract was subjected to vacuum-filtration, and then the filtrated organic solvent was concentrated. The resultant product was separated by column chromatography, with the result that desired intermediate B was obtained with a yield of 57%.

Synthesis of Intermediate C

The intermediate B obtained from the above step and triphenylphosphine were dissolved in o-DCB (o-dichlorobenzene), followed by reflux for 24 hours. Upon completion of the reaction, the solvent was removed using vacuum distillation, and then the concentrated product was separated by column chromatography, with the result that desired intermediate C was obtained with a yield of 61%.

Synthesis of Intermediate D

The intermediate C obtained from the above step, iodobenzene, Pd$_2$(dba)$_3$, P(tBu)$_3$, and NaOtBu were dissolved in a toluene solvent, followed by reflux for 6 hours at 110° C. Upon completion of the reaction, the reaction product was subjected to vacuum filtration through Celite and silica gel by using a hot toluene solvent. The temperature of the filtrate was cooled to room temperature, and then the precipitated product was recrystallized again using toluene and acetone, with the result that desired intermediate D was obtained by a yield of 77%.

Synthesis of Compound 1-15

The intermediate D obtained from the above step, bis(9,9-dimethyl-9H-fluorene-2-yl)amine, Pd$_2$(dba)$_3$, P(tBu)$_3$, and NaOtBu were dissolved in a toluene solvent, followed by reflux for 24 hours at 110° C. Upon completion of the reaction, the reaction product was subjected to vacuum filtration through Celite and silica gel by using a hot toluene solvent. The temperature of the filtrate was cooled to room temperature, and then the precipitated product was recrystallized again using toluene and acetone, with the result that desired compound 1-15 was obtained by a yield of 68%.

2. Synthesis Method of Compounds 2-10

[Reaction Scheme 2]

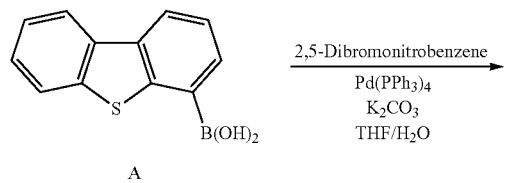

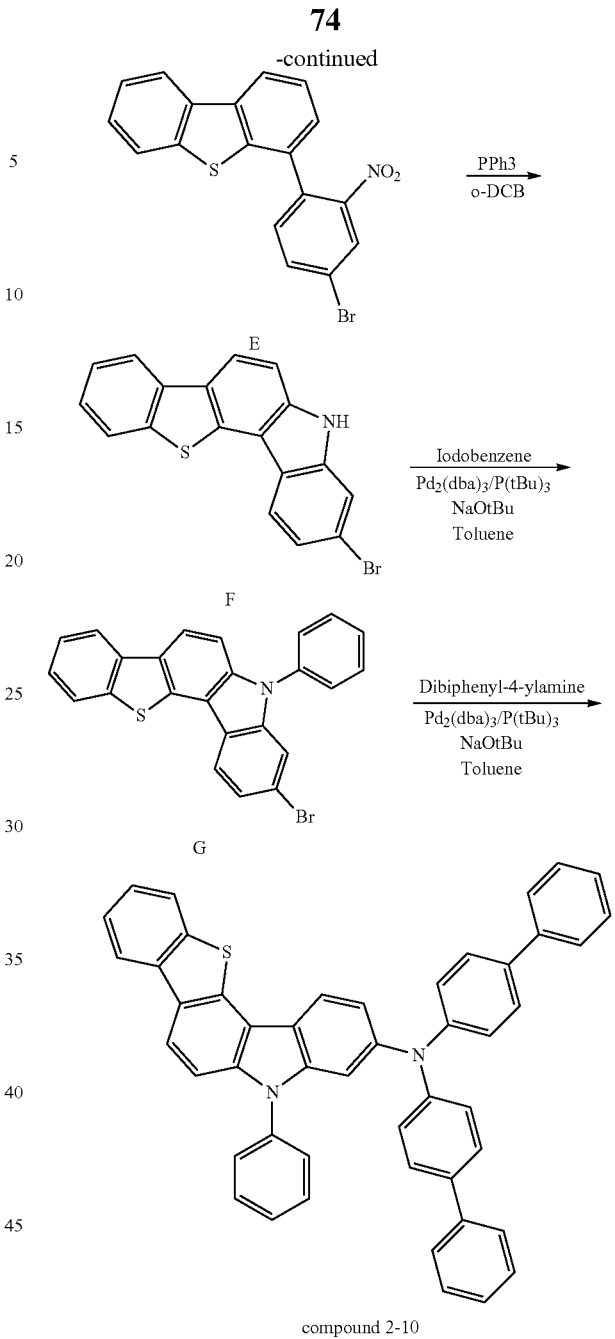

compound 2-10

With reference to Reaction Scheme 2 above, preparation methods of intermediates E to G and a preparation method of compound 2-10 will be described below Synthesis Method of Intermediate E The intermediate A obtained from the above step, 2,5-dibromonitrobenzene, P$_d$(PPh$_3$)$_4$, and potassium carbonate (K$_2$CO$_3$) were dissolved in tetrahydrofuran (THF) and a small amount of water, followed by reflux for 24 hours. Upon completion of the reaction, the reaction product was cooled to room temperature, extracted with dichloromethane (CH$_2$Cl$_2$), and washed with water. A small amount of water was removed from the extract by anhydrous magnesium sulfate (MgSO$_4$), the extract was subjected to vacuum-filtration, and then the filtrated organic solvent was concentrated. The resultant product was separated by column chromatography, with the result that desired intermediate E was obtained with a yield of 68%.

Synthesis of Intermediate F

The intermediate E obtained from the above step and triphenylphosphine were dissolved in o-DCB (o-dichlorobenzene), followed by reflux for 24 hours. Upon completion of the reaction, the solvent was removed using vacuum distillation, and then the concentrated product was separated by column chromatography, with the result that desired intermediate F was obtained with a yield of 71%.

Synthesis of Intermediate G

The intermediate F obtained from the above step, iodobenzene, Pd$_2$(dba)$_2$, P(tBu)$_3$, and NaOtBu were dissolved in a toluene solvent, followed by reflux for 6 hours at 110° C. Upon completion of the reaction, the reaction product was subjected to vacuum filtration through Celite and silica gel by using a hot toluene solvent. The temperature of the filtrate was cooled to room temperature, and then the precipitated product was recrystallized again using toluene and acetone, with the result that desired intermediate G was obtained by a yield of 80%.

Synthesis of Compound 2-10

The intermediate G obtained from the above step, diphenyl-4-ylamine, Pd$_2$(dba)$_3$, P(tBu)$_3$, and NaOtBu were dissolved in a toluene solvent, followed by reflux for 24 hours at 110° C. Upon completion of the reaction, the reaction product was subjected to vacuum filtration through Celite and silica gel by using a hot toluene solvent. The temperature of the filtrate was cooled to room temperature, and then the precipitated product was recrystallized again using toluene and acetone, with the result that desired compound 2-10 was obtained by a yield of 72%.

3. Synthesis Method of Compound 3-14

[Reaction Scheme 3]

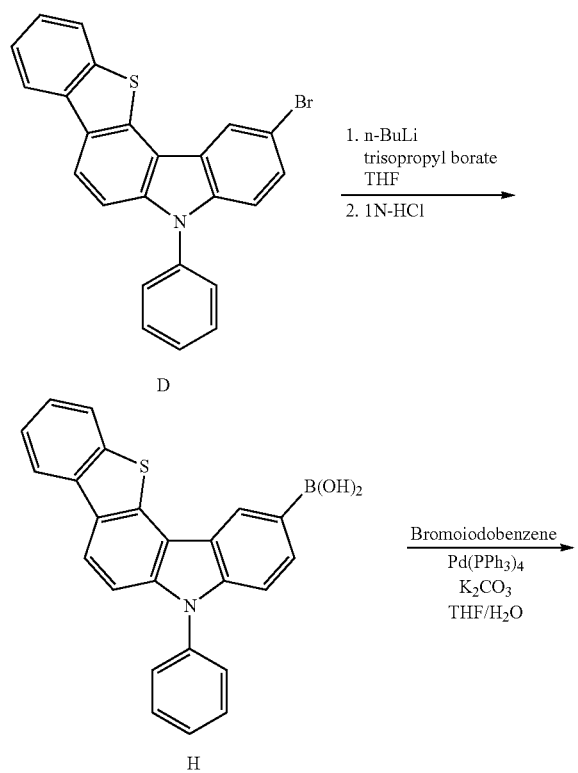

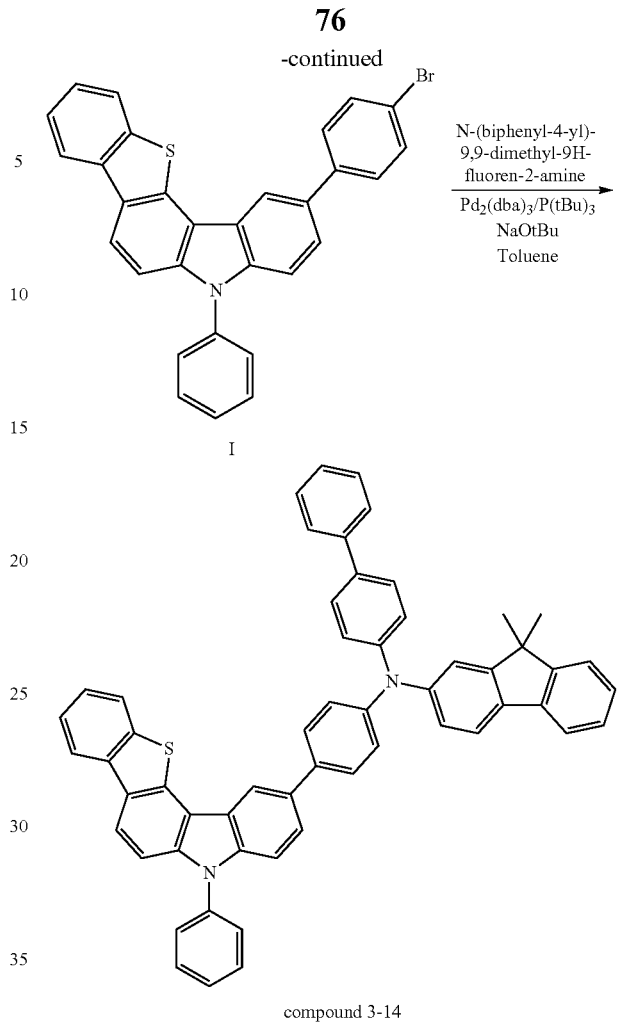

compound 3-14

With reference to Reaction Scheme 3 above, preparation methods of intermediates H and I and a preparation method of compound 3-14 will be described below.

Synthesis of Intermediate H

The intermediate D obtained from the above step was dissolved in anhydrous tetrahydrofurane (THF), and the temperature of the reactants was lowered to −78° C. n-BuLi (2.5 M in hexane) was slowly added dropwise to the reactants, and then the reactants were stirred for 1 hour at 0° C. Subsequently, the temperature of the reactants was lowered to −78° C., and a triisopropyl borate solution dissolved in tetrahydrofuran (THF) was added dropwise to the reactants, followed by stirring for 12 hours at room temperature. Upon completion of the reaction, the reaction product was added with 1N—HCl aqueous solution, stirred for 30 minutes, and then extracted with ether. A small amount of water was removed from the extract by anhydrous magnesium sulfate (MgSO$_4$), the extract was subjected to vacuum-filtration, and then the filtrated organic solvent was concentrated. The resultant product was separated by column chromatography, with the result that desired intermediate H was obtained with a yield of 57%.

Synthesis of Intermediate I

The intermediate H obtained from the above step, bromoiodobenzene, Pd(PPh$_2$)$_4$, and potassium carbonate (K$_2$CO$_3$) were dissolved in tetrahydrofuran (THF) and a small amount of water, followed by reflux for 12 hours. Upon completion of the reaction, the reaction product was cooled to room temperature, extracted with dichloromethane (CH$_2$Cl$_2$), and washed with water. A small amount of water was removed from the extract by anhydrous magnesium sulfate (MgSO$_4$), the extract was subjected to vacuum-filtration, and then the filtrated organic solvent was concentrated. The resultant product was separated by column chromatography, with the result that desired intermediate I was obtained with a yield of 63%.

Synthesis of Compound 3-14

The intermediate I obtained from the above step, N-(biphenyl-4-yl)-9,9-dimethyl-9H-fluorene-2-amine, Pd$_2$(dba)$_2$, P(tBu)$_2$, and NaOtBu were dissolved in a toluene solvent, followed by reflux for 24 hours at 110° C. Upon completion of the reaction, the reaction product was subjected to vacuum filtration through Celite and silica gel by using a hot toluene solvent. The temperature of the filtrate was cooled to room temperature, and then the precipitated product was recrystallized again using toluene and acetone, with the result that desired compound 3-14 was obtained by a yield of 68%.

4. Synthesis Method of Compound 4-8

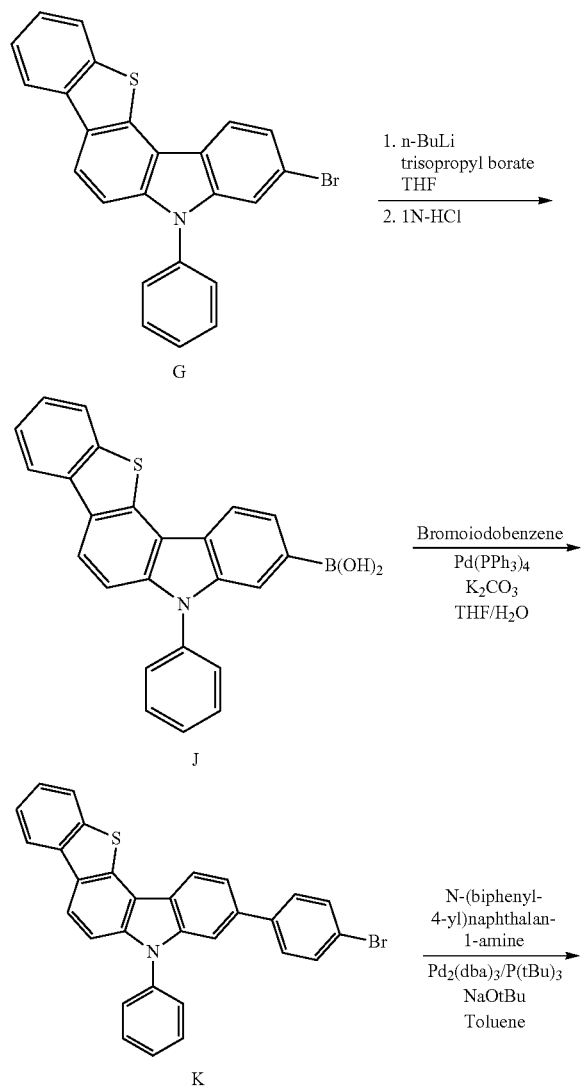

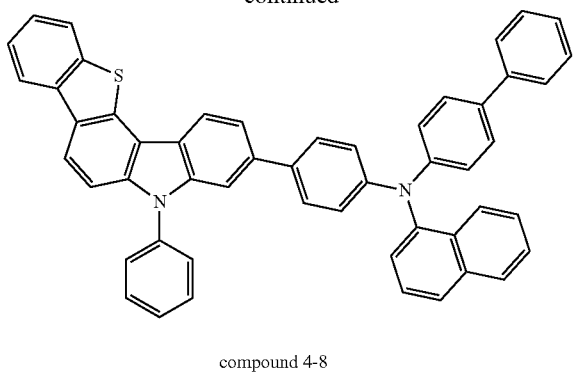

compound 4-8

With reference to Reaction Scheme 4 above, preparation methods of intermediates J and K and a preparation method of compound 4-8 will be described below.

Synthesis of Intermediate J

The intermediate G obtained from the above step was dissolved in anhydrous tetrahydrofurane (THF), and the temperature of the reactants was lowered to −78° C. n-BuLi (2.5 M in hexane) was slowly added dropwise to the reactants, and then the reactants were stirred for 1 hour at 0° C. Subsequently, the temperature of the reactants was lowered to −78° C., and a triisopropyl borate solution dissolved in tetrahydrofuran (THF) was added dropwise to the reactants, followed by stirring for 12 hours at room temperature. Upon completion of the reaction, the reaction product was added with 1N—HCl aqueous solution, stirred for 30 minutes, and then extracted with ether. A small amount of water was removed from the extract by anhydrous magnesium sulfate (MgSO$_4$), the extract was subjected to vacuum-filtration, and then the filtrated organic solvent was concentrated. The resultant product was separated by column chromatography, with the result that desired intermediate J was obtained with a yield of 61%.

Synthesis of Intermediate K

The intermediate J obtained from the above step, bromoiodobenzene, Pd(PPh$_3$)$_4$, and potassium carbonate (K$_2$CO$_3$) were dissolved in tetrahydrofuran (THF) and a small amount of water, followed by reflux for 12 hours. Upon completion of the reaction, the reaction product was cooled to room temperature, extracted with dichloromethane (CH$_2$Cl$_2$), and washed with water. A small amount of water was removed from the extract by anhydrous magnesium sulfate (MgSO$_4$), the extract was subjected to vacuum-filtration, and then the filtrated organic solvent was concentrated. The resultant product was separated by column chromatography, with the result that desired intermediate K was obtained with a yield of 66%.

Synthesis of Compound 4-8

The intermediate K obtained from the above step, N-(biphenyl-4-yl)naphthalene-1-amine, Pd$_2$(dba)$_3$, P(tBu)$_3$, and NaOtBu were dissolved in a toluene solvent, followed by reflux for 24 hours at 110° C. Upon completion of the reaction, the reaction product was subjected to vacuum filtration through Celite and silica gel by using a hot toluene solvent. The temperature of the filtrate was cooled to room temperature, and then the precipitated product was recrystallized again using toluene and acetone, with the result that desired compound 4-8 was obtained by a yield of 65%.

5. Synthesis Method of Compound 5-1

[Reaction Scheme 5]

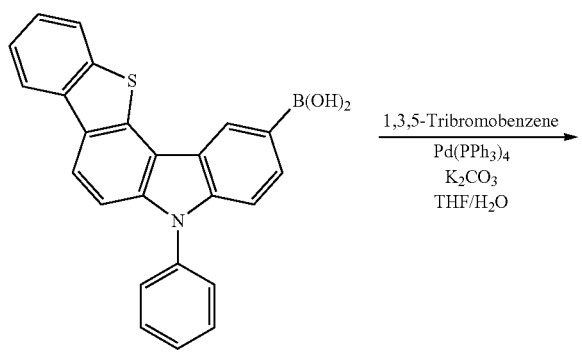

H

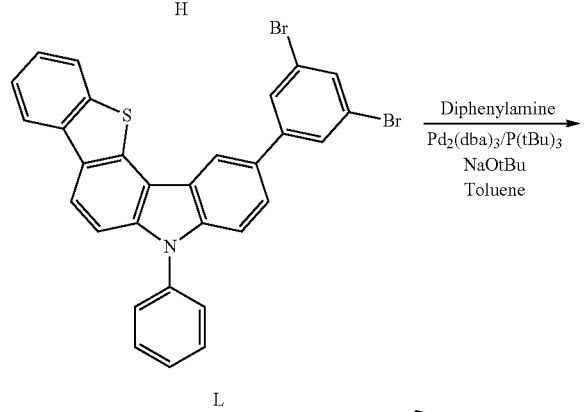

L

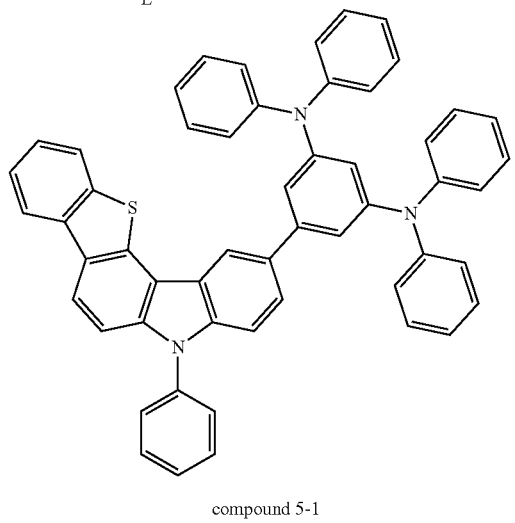

compound 5-1

With reference to Reaction Scheme 5 above, preparation methods of intermediate L and compound 5-1 will be described below.

Synthesis of Intermediate L

The intermediate H obtained from the above step, 1,3,5-tribromobenzene, Pd(PPh$_3$)$_4$, and potassium carbonate (K$_2$CO$_3$) were dissolved in tetrahydrofuran (THF) and a small amount of water, followed by reflux for 12 hours. Upon completion of the reaction, the reaction product was cooled to room temperature, extracted with dichloromethane (CH$_2$Cl$_2$), and washed with water. A small amount of water was removed from the extract by anhydrous magnesium sulfate (MgSO$_4$), the extract was subjected to vacuum-filtration, and then the filtrated organic solvent was concentrated. The resultant product was separated by column chromatography, with the result that desired intermediate K was obtained with a yield of 42%.

Synthesis of Compound 5-1

The intermediate L obtained from the above step, diphenylamine, Pd$_2$(dba)$_3$, P(tBu)$_3$, and NaOtBu were dissolved in a toluene solvent, followed by reflux for 24 hours at 110° C. Upon completion of the reaction, the reaction product was subjected to vacuum filtration through Celite and silica gel by using a hot toluene solvent. The temperature of the filtrate was cooled to room temperature, and then the precipitated product was recrystallized again using toluene and acetone, with the result that desired compound 5-1 was obtained by a yield of 69%.

6. Synthesis Method of Compound 6-3

[Reaction Scheme 6]

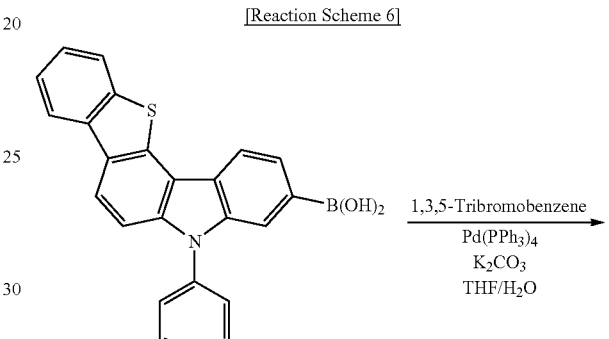

J

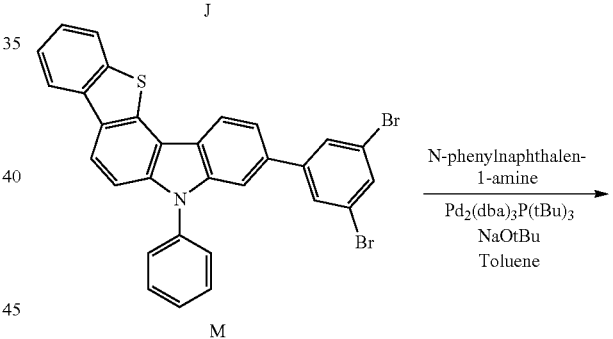

M

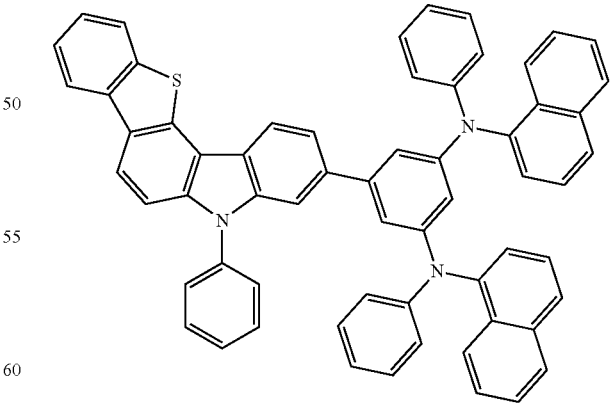

compound 6-3

With reference to Reaction Scheme 6 above, preparation methods of intermediate M and compound 6-3 will be described below.

Synthesis of Intermediate M

The intermediate J obtained from the above step, 1,3,5-tribromobenzene, Pd(PPh$_3$)$_4$, and potassium carbonate (K$_2$CO$_3$) were dissolved in tetrahydrofuran (THF) and a small amount of water, followed by reflux for 12 hours. Upon completion of the reaction, the reaction product was cooled to room temperature, extracted with dichloromethane (CH$_2$Cl$_2$), and washed with water. A small amount of water was removed from the extract by anhydrous magnesium sulfate (MgSO$_4$), the extract was subjected to vacuum-filtration, and then the filtrated organic solvent was concentrated. The resultant product was separated by column chromatography, with the result that desired intermediate M was obtained with a yield of 49%.

Synthesis of Compound 6-3

The intermediate M obtained from the above step, N-phenylnaphthalene-1-amine, Pd$_2$(dba)$_2$, P(tBu)$_3$, and NaOtBu were dissolved in a toluene solvent, followed by reflux for 24 hours at 110° C. Upon completion of the reaction, the reaction product was subjected to vacuum filtration through Celite and silica gel by using a hot toluene solvent. The temperature of the filtrate was cooled to room temperature, and then the precipitated product was recrystallized again using toluene and acetone, with the result that desired compound 6-3 was obtained by a yield of 68%.

Meanwhile, since there are a wide range of substituents for each of R$_1$ to R$_6$, X, Ar, Y, and Z of compounds represented by Formula 1, Synthesis Examples of only representative compounds of the compounds represented by Formula 1 have been illustratively described. However, other compounds represented by Formula 1 than those illustratively described may also form a part of this specification.

Fabrication and Evaluation of Organic EL Element

An OLED was fabricated according to a conventional method by using each of the synthesized compounds 1-15, 2-10, 3-14, 4-8, 5-1, and 6-3 as a hole transport material. Each OLED was fabricated by first forming an ITO layer (anode) on a glass substrate and then sequentially depositing a hole injection layer (hole injection layer material: 2-TNATA) with a thickness of 600 Å, a hole transport layer (hole transport layer material: synthesized compound) with a thickness of 300 Å, a light emitting layer (doped with 7% of BD-052X: Here, BD-052X was a blue fluorescent dopant and 9,10-di(naphthalene-2-yl)anthracene (AND) was used as a light emitting host material) with a thickness of 450 Å, an electron transport layer (electron transport layer material: tris(8-quinolinolato)aluminum (Alq$_3$)) with a thickness of 250 Å, an electron injection layer (electron injection later material: LiF) with a thickness of 10 Å, and an aluminum cathode with a thickness of 1500 Å.

Comparative Test Example 1

For the purpose of comparison with the synthesized compounds, an OLED with the same structure was manufactured using a compound represented by Formula 14 below as a hole transport layer material, instead of the inventive compound.

[Formula 14]

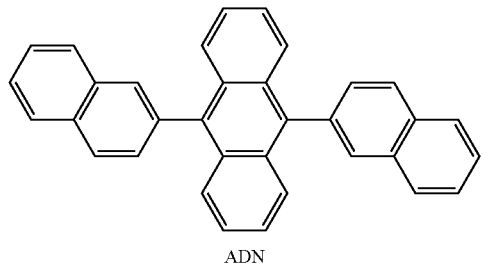

ADN

TABLE 1

| | hole transport layer material | voltage (V) | current density (mA/cm$^2$) | luminous efficiency (cd/A) | chromaticity coordinate (x, y) |
|---|---|---|---|---|---|
| Example 1 | compound 1-15 | 5.4 | 13.92 | 8.7 | (0.15, 0.14) |
| Example 2 | compound 2-10 | 6.1 | 13.74 | 8.5 | (0.15, 0.15) |
| Example 3 | compound 3-14 | 5.1 | 14.11 | 9.0 | (0.15, 0.15) |
| Example 4 | compound 4-8 | 6.2 | 14.06 | 8.7 | (0.15, 0.14) |
| Example 5 | compound 5-1 | 5.5 | 13.92 | 8.8 | (0.15, 0.14) |
| Example 6 | compound 6-3 | 6.0 | 13.88 | 8.4 | (0.15, 0.15) |
| Comparative Example 1 | ADN | 7.1 | 13.47 | 7.5 | (0.15, 0.15) |

As seen from the results noted in Table 1, an OLED using the inventive OLED material not only has high efficiency and improved color purity, but can also significantly lower driving voltage. Thus, the inventive OLED material can significantly improve the luminous efficiency and life span of an OLED using the inventive material.

It is obvious that even though the inventive compounds are used in other organic material layers of an OLED, for example, an emitting layer, an emission assisting layer, an electron injection layer, an electron transport layer, and a hole injection layer, in addition to a hole transport layer, the same effects can be obtained.

Since terms "comprising," "including," "having", and the like described mean that one or more corresponding components may exist unless they are specifically described to the contrary, it shall be construed that one or more other components can be included. All of the terminologies containing one or more technical or scientific terminologies have the same meanings that persons skilled in the art understand ordinarily unless they are defined otherwise. A term ordinarily used like that defined by a dictionary shall be construed that it has a meaning equal to that in the context of a related description, and shall not be construed in an ideal or excessively formal meaning unless it is clearly defined in the present specification.

Although exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed in the present invention is intended to illustrate the scope of the technical idea of the present invention, and the scope of the present invention is not limited by the embodiment. The scope of the present invention shall be construed on the basis of the accompanying claims, and it shall be construed that all of the technical ideas included within the scope equivalent to the claims belong to the present invention.

CROSS-REFERENCE TO RELATED APPLICATION

This application claims priority from and the benefit under 35 U.S.C. §119(a) of Korean Patent Application No. 10-2010-0049325, filed on May 26, 2010, which is hereby incorporated by reference for all purposes as if fully set forth herein. Further, this application claims the benefit of priority in other countries than U.S., which are hereby incorporated by reference herein.

What is claimed is:

1. A compound represented by Formula below:

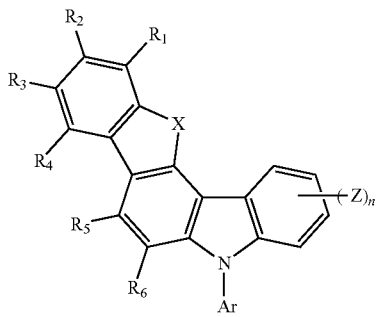

wherein $R_1$, $R_2$, $R_3$, $R_4$, $R_5$, and $R_6$ are each independently a hydrogen atom, a halogen atom, a cyano group, an alkoxy group, a thiol group, a substituted or unsubstituted C1 to C50 alkyl group, a substituted or unsubstituted C1 to C50 alkoxy group, a substituted or unsubstituted C1 to C50 alkenyl group, a substituted or unsubstituted C5 to C60 arylene group, a substituted or unsubstituted C5 to C60 aryl group, a substituted or unsubstituted C5 to C60 aryloxy group, a substituted or unsubstituted C1 to C50 alkyl group including at least one of sulfur (S), nitrogen (N), oxygen (O), phosphorous (P), and silicon (Si), a substituted or unsubstituted C5 to C60 heteroaryl group including at least one of sulfur (S), nitrogen (N), oxygen (O), phosphorous (P) and silicon (Si), or a substituted or unsubstituted C5 to C60 heteroaryloxy group including at least one of sulfur (S), nitrogen (N), oxygen (O), phosphorous (P) and silicon (Si);

X is sulfur (S), oxygen (O), or silicon (Si);

Ar is a hydrogen atom, a substituted or unsubstituted C1 to C50 alkyl group, a substituted or unsubstituted C1 to C50 alkenyl group, a substituted or unsubstituted C5 to C60 arylene group, a substituted or unsubstituted C5 to C60 aryl group, a substituted or unsubstituted C5 to C60 aryloxy group, a substituted or unsubstituted C1 to C50 alkyl group including at least one of sulfur (S), nitrogen (N), oxygen (O), phosphorous (P), and silicon (Si), a substituted or unsubstituted C5 to C60 heteroaryl group including at least one of sulfur (S), nitrogen (N), oxygen (O), phosphorous (P) and silicon (Si), or a substituted or unsubstituted C5 to C60 heteroaryloxy group including at least one of sulfur (S), nitrogen (N), oxygen (O), phosphorous (P) and silicon (Si);

Y is a substituted or unsubstituted C1 to C50 alkyl group, a substituted or unsubstituted C1 to C50 alkenyl group, a substituted or unsubstituted C5 to C60 arylene group, a substituted or unsubstituted C5 to C60 aryl group, a substituted or unsubstituted C5 to C60 aryloxy group, a substituted or unsubstituted C1 to C50 alkyl group including at least one of sulfur (S), nitrogen (N), oxygen (O), phosphorous (P), and silicon (Si), a substituted or unsubstituted C5 to C60 heteroaryl group including at least one of sulfur (S), nitrogen (N), oxygen (O), phosphorous (P) and silicon (Si), or a substituted or unsubstituted C5 to C60 heteroaryloxy group including at least one of sulfur (S), nitrogen (N), oxygen (O), phosphorous (P) and silicon (Si);

n is 1 or 2;

Z is S, $NR_7R_8$, $OR_9$, $PR_{10}R_{11}$ or $POR_{10}R_{11}$, or $SiR_{12}$ wherein $R_7$, $R_8$, $R_9$, $R_{10}$, $R_{11}$, and $R_{12}$ are each independently a substituted or unsubstituted C5 to C60 aryl group or a substituted or unsubstituted C5 to C60 heteroaryl group including at least one of sulfur (S), nitrogen (N), oxygen (O), phosphorous (P) and silicon (Si), with the proviso that $R_7$ and $R_8$ do not bond to each other to form a ring structure.

2. The compound as claimed in claim 1, wherein at least one couple of $R_1$ and $R_2$, $R_2$ and $R_3$, $R_3$ and $R_4$, and $R_5$ and $R_6$ bond to each other to form a ring structure.

3. The compound as claimed in claim 1, wherein the compound is represented by one of Formulas below:

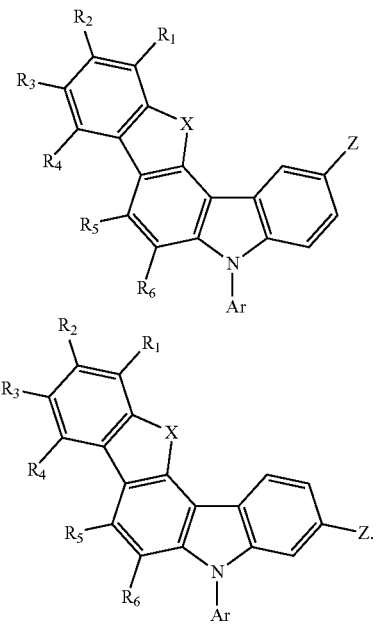

4. An organic electrical element comprising one or more organic material layers comprising the compound as claimed in claim 1.

5. The organic electrical element as claimed in claim 4, wherein said one or more organic material layers are formed to comprise the compound by a soluble process.

6. The organic electrical element as claimed in claim 4, wherein the organic electrical element comprises an organic light emitting diode (OLED) having a structure in which a first electrode, the one or more organic material layers, and a second electrode are sequentially laminated.

7. The organic electrical element as claimed in claim 6, wherein the one or more organic material layers comprise any one of a hole injection layer, a hole transport layer, a light emitting layer, an electron transport layer, an electron injection layer, and a combination thereof.

8. The organic electrical element as claimed in claim 6, wherein the organic material layers comprise a hole injection layer, and the compound is used as a hole transport material in the hole transport layer.

9. A terminal comprising a display device, which comprises the organic electrical element as claimed in claim 6, and a control unit for driving the display device.

10. The terminal as claimed in claim 9, wherein the organic electrical element comprises any one of an organic light emitting diode (OLED), an organic solar cell, an organic photo conductor (OPC) drum, and an organic transistor (organic TFT).

* * * * *